(12) United States Patent
Woo et al.

(10) Patent No.: US 8,721,962 B2
(45) Date of Patent: May 13, 2014

(54) METHODS, DEVICES, COMPOSITIONS AND SYSTEMS FOR IMPROVED SCENT DELIVERY

(71) Applicant: The Procter & Gamble Company, Cincinnati, OH (US)

(72) Inventors: Ricky Ah-Man Woo, Hamilton, OH (US); Mario Alonso, Loveland, OH (US); John Philip Hecht, West Chester, OH (US); Steven Reece, Hamilton, OH (US); Frank Andrej Kvietok, Cincinnati, OH (US); Eileen Marie St. Pierre, Cincinnati, OH (US); Zaiyou Liu, West Chester, PA (US); Christine Marie Readnour, Ft. Mitchell, KY (US); Carl Eric Kaiser, Lebanon, OH (US); Susan Eleanor Baillely, Cincinnati, OH (US); Sion Agami, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/713,209

(22) Filed: Dec. 13, 2012

(65) Prior Publication Data
US 2013/0134233 A1    May 30, 2013

Related U.S. Application Data

(63) Continuation of application No. 13/363,454, filed on Feb. 1, 2012, now Pat. No. 8,349,251, which is a continuation of application No. 12/269,856, filed on (Continued)

(51) Int. Cl.
*A61L 9/00* (2006.01)
*A62B 7/08* (2006.01)

(52) U.S. Cl.
USPC ................... 422/5; 422/123; 422/125

(58) Field of Classification Search
USPC ............................................. 422/5
See application file for complete search history.

(56) References Cited

U.S. PATENT DOCUMENTS

| 1,944,821 | A | 1/1934 | Blaise |
| 2,176,345 | A | 10/1939 | Hurwitt |

(Continued)

FOREIGN PATENT DOCUMENTS

| CA | 2329605 | 7/2001 |
| EP | 0238 983 A2 | 9/1987 |

(Continued)

OTHER PUBLICATIONS

Corrected Request for Inter Partes Reexamination of US Patent 7,223,361 B2, Sep. 15, 2008.

(Continued)

*Primary Examiner* — Regina M Yoo
(74) *Attorney, Agent, or Firm* — Amy I Ahn-Roll

(57) ABSTRACT

Systems, devices, methods, and compositions that improve the scent perception for a user. Improved scent perception is achieved by presenting alternating scents and by varying levels of output of scents, as well as by minimizing device clogging, thereby improving evaporation profiles.

16 Claims, 22 Drawing Sheets

Related U.S. Application Data

Nov. 12, 2008, now Pat. No. 8,119,064, which is a continuation of application No. 10/820,284, filed on Apr. 8, 2004, now abandoned, and a continuation of application No. 10/417,456, filed on Apr. 16, 2003, now abandoned, and a continuation of application No. 10/417,462, filed on Apr. 16, 2003, now abandoned, said application No. 10/417,456 is a continuation-in-part of application No. 09/904,019, filed on Jul. 12, 2001, now abandoned, said application No. 10/417,462 is a continuation-in-part of application No. 09/904,019, which is a continuation-in-part of application No. 09/730,226, filed on Dec. 5, 2000, now Pat. No. 6,581,915, and a continuation-in-part of application No. 09/730,261, filed on Dec. 5, 2000, now abandoned, and a continuation-in-part of application No. 09/730,333, filed on Dec. 5, 2000, now abandoned.

(60) Provisional application No. 60/507,772, filed on Oct. 1, 2003, provisional application No. 60/507,807, filed on Oct. 1, 2003.

(56) References Cited

U.S. PATENT DOCUMENTS

| | | |
|---|---|---|
| 2,611,068 A | 9/1952 | Wellens |
| 2,715,056 A | 8/1955 | Wilson |
| 2,898,649 A | 8/1959 | Murray |
| 3,028,100 A | 4/1962 | Xenakis et al. |
| 3,091,396 A | 5/1963 | Curtin |
| 3,431,393 A | 3/1969 | Katsuda |
| 3,440,589 A | 4/1969 | Minks |
| 3,724,756 A | 4/1973 | Maltenfort |
| 3,780,260 A | 12/1973 | Elsner |
| 4,166,087 A | 8/1979 | Cline et al. |
| 4,181,255 A | 1/1980 | Cort |
| 4,346,059 A | 8/1982 | Spector |
| 4,467,177 A | 8/1984 | Zobele |
| 4,494,926 A | 1/1985 | Riha |
| 4,556,539 A | 12/1985 | Spector |
| 4,595,564 A | 6/1986 | Spector et al. |
| 4,621,768 A | 11/1986 | Lhoste et al. |
| 4,629,604 A | 12/1986 | Spector |
| 4,631,387 A | 12/1986 | Glucksman |
| 4,663,315 A | 5/1987 | Hasegawa et al. |
| 4,695,434 A | 9/1987 | Spector |
| 4,739,928 A | 4/1988 | O'Neil |
| 4,745,705 A | 5/1988 | Yamamoto et al. |
| 4,769,528 A | 9/1988 | Von Philipp et al. |
| 4,795,883 A | 1/1989 | Glucksman et al. |
| 4,798,935 A | 1/1989 | Pezaris |
| 4,804,821 A | 2/1989 | Glucksman |
| 4,857,240 A | 8/1989 | Kearnes et al. |
| 4,913,350 A | 4/1990 | Purzycki |
| 4,968,487 A | 11/1990 | Yamamoto et al. |
| 5,000,383 A | 3/1991 | van der Heijden |
| 5,038,394 A | 8/1991 | Hasegawa et al. |
| 5,095,647 A | 3/1992 | Zobele et al. |
| 5,114,625 A | 5/1992 | Gibson |
| 5,115,975 A | 5/1992 | Shilling |
| 5,175,791 A | 12/1992 | Muderlak et al. |
| 5,222,186 A | 6/1993 | Schimanski et al. |
| 5,264,681 A | 11/1993 | Nozaki et al. |
| 5,290,546 A | 3/1994 | Hasegawa et al. |
| 5,402,517 A | 3/1995 | Gillett et al. |
| 5,622,314 A | 4/1997 | Eason |
| 5,647,053 A | 7/1997 | Schroeder et al. |
| 5,669,767 A | 9/1997 | Bureau et al. |
| 5,725,152 A | 3/1998 | Akyu |
| 5,727,186 A | 3/1998 | Shervington et al. |
| 5,749,519 A | 5/1998 | Miller |
| 5,749,520 A | 5/1998 | Martin et al. |
| 5,840,246 A | 11/1998 | Hammons et al. |
| 5,875,968 A | 3/1999 | Miller et al. |
| 5,903,710 A | 5/1999 | Wefler et al. |
| 5,906,298 A | 5/1999 | Ward |
| 5,909,845 A | 6/1999 | Greatbatch et al. |
| 5,945,094 A | 8/1999 | Martin et al. |
| 5,976,503 A | 11/1999 | Martin et al. |
| 6,044,202 A | 3/2000 | Junkel |
| 6,085,026 A | 7/2000 | Hammons et al. |
| 6,152,379 A | 11/2000 | Sorgenfrey |
| 6,236,807 B1 | 5/2001 | Ruffolo et al. |
| 6,278,840 B1 | 8/2001 | Millan |
| 6,285,830 B1 | 9/2001 | Millan |
| 6,354,513 B1 | 3/2002 | Millan |
| 6,361,752 B1 | 3/2002 | Demarest et al. |
| 6,371,451 B1 | 4/2002 | Choi |
| 6,446,384 B2 | 9/2002 | Pedrotti et al. |
| 6,446,583 B2 | 9/2002 | Vieira |
| 6,465,420 B1 | 10/2002 | Perring et al. |
| 6,466,739 B2 | 10/2002 | Ambrosi et al. |
| 6,487,367 B2 | 11/2002 | Vieira |
| 6,501,906 B2 | 12/2002 | Vieira |
| 6,563,091 B2 | 5/2003 | Vieira |
| 6,567,613 B2 | 5/2003 | Rymer |
| RE38,150 E | 6/2003 | Greatbatch et al. |
| 6,580,875 B2 | 6/2003 | Rymer |
| 6,603,924 B2 | 8/2003 | Brown et al. |
| 6,619,560 B1 | 9/2003 | Chun |
| 6,659,301 B2 | 12/2003 | Fellows et al. |
| 6,697,571 B2 | 2/2004 | Triplett et al. |
| 2001/0012495 A1 | 8/2001 | Furner et al. |
| 2001/0020450 A1 | 9/2001 | Vieira |
| 2002/0066967 A1 | 6/2002 | Bartsch et al. |
| 2002/0068010 A1 | 6/2002 | Laudamiel-Pellet et al. |
| 2002/0076214 A1 | 6/2002 | Vieira |
| 2002/0090318 A1 | 7/2002 | Challand et al. |
| 2002/0136886 A1 | 9/2002 | He et al. |
| 2002/0159916 A1 | 10/2002 | Whitby et al. |
| 2003/0005620 A1 | 1/2003 | Ananth et al. |
| 2004/0028551 A1 | 2/2004 | Kvietok et al. |
| 2004/0033171 A1 | 2/2004 | Kvietok et al. |
| 2004/0151747 A1 | 8/2004 | Davis et al. |
| 2009/0185950 A1 | 7/2009 | Woo et al. |
| 2012/0126025 A1 | 5/2012 | Woo et al. |

FOREIGN PATENT DOCUMENTS

| | | |
|---|---|---|
| EP | 0 736 248 A1 | 10/1996 |
| EP | 0 740 941 A1 | 11/1996 |
| EP | 0 511 853 B1 | 12/1997 |
| EP | 0 911 041 A2 | 4/1998 |
| EP | 0 962 132 A1 | 12/1999 |
| EP | 0 911 041 A3 | 9/2000 |
| EP | 0 942 648 B9 | 1/2002 |
| EP | 0 943 344 B1 | 9/2002 |
| EP | 1 260 255 | 11/2002 |
| EP | 0 962 132 B1 | 5/2003 |
| ES | 1 015 255 | 6/1991 |
| GB | 2279010 | 12/1994 |
| GB | 2 358 802 A | 8/2001 |
| GB | 2 375 710 A | 11/2002 |
| JP | 09047499 A | 2/1997 |
| JP | 11000391 A | 1/1999 |
| WO | WO 90/13359 A1 | 11/1990 |
| WO | WO 94/15650 A1 | 7/1994 |
| WO | WO 98/00177 | 1/1998 |
| WO | WO 98/19526 A1 | 5/1998 |
| WO | WO 98/58692 A1 | 12/1998 |
| WO | WO 00/48922 A1 | 8/2000 |
| WO | WO 01/05442 A1 | 1/2001 |
| WO | WO 02/17977 A3 | 3/2002 |
| WO | WO 02/060494 A1 | 8/2002 |
| WO | WO 03/103387 A2 | 12/2003 |
| WO | WO 2004/002542 A1 | 1/2004 |

OTHER PUBLICATIONS

Inter Partes Reexamination Communication for U.S. Appl. No. 95/000,377, filed Oct. 2, 2008.

(56) References Cited

OTHER PUBLICATIONS

Office Action for U.S. Appl. No. 95/000,377, date mailed Nov. 20, 2008.
Response to Notice Re Defective Paper in Inter Partes Reexamination for Application No. 95/000,377, dated Feb. 25, 2009.
Comments by Third Party Requester, for U.S. Appl. No. 95/000,377, dated Mar. 25, 2009.
Office Action for U.S. Appl. No. 95/000,377, date mailed Dec. 9, 2009.
Response to Office Action—Closing for U.S. Appl. No. 95/000,377, dated Jan. 11, 2010.
Comments by Third Party Requester, for U.S. Appl. No. 95/000,377, filed Feb. 10, 2010.
Office Action for U.S. Appl. No. 95/000,377, dated Mar. 22, 2010.
Response to Office Action—Closing for U.S. Appl. No. 95/000,377, dated Apr. 22, 2010.
Comments by Third Party Requester, for U.S. Appl. No. 95/000,377, dated May 24, 2010.
Appeal Brief for U.S. Appl. No. 95/000,377, filed Sep. 16, 2010.
Comments by Third Party Requester, for U.S. Appl. No. 95/000,377, filed Oct. 13, 2010.
Office Action for U.S. Appl. No. 95/000,377, dated Nov. 24, 2010.
Response to Office Action—Closing for U.S. Appl. No. 95/000,377, dated Dec. 22, 2010.
Comments by Third Party Requester, for U.S. Appl. No. 95/000,377, filed Jan. 21, 2011.
Office Action for U.S. Appl. No. 95/000,377, dated Feb. 4, 2011.
Response to Office Action—Patent Owner Appeal Brief for U.S. Appl. No. 95/000,377, dated May 4, 2011.
Office Action—Examiner's Answer for U.S. Appl. No. 95/000,377, dated Jun. 16, 2011.
Response to Office Action—Patent Owner Rebuttal Brief for U.S. Appl. No. 95/000,377, dated Jul. 15, 2011.
Comments by Third Party Requester, for U.S. Appl. No. 95/000,377, dated Jul. 18, 2011.
Office Action—Board of Patent Appeals & Interferences Decision, for U.S. Appl. No. 95/000,377, dated Mar. 28, 2012.
Comments by Third Party Requester, Request for Rehearing, for U.S. Appl. No. 95/000,377, dated Apr. 30, 2012.
Comments by Patent Owner, Comments on Request for Rehearing, for U.S. Appl. No. 95/000,377, dated May 30, 2012.

METHODS, DEVICES, COMPOSITIONS AND SYSTEMS FOR IMPROVED SCENT DELIVERY

FIELD OF THE INVENTION

The present invention relates to methods, devices, systems, and compositions for improved scent delivery. The invention delivers a scent experience to the user, which diminishes less over a period of time, as compared with other methods, devices, systems, and compositions. The invention thus provides the user with a scent experience that is more noticeable for a longer period.

BACKGROUND OF THE INVENTION

It is generally known to use an electrical device to evaporate a perfume and/or fragrance composition into a space, particularly a domestic space, e.g., a living room, to provide a pleasant aroma. There are a variety of such devices on sale, including for example the AIRWICK® Diffuser ACTIF® (manufactured by Reckitt Benckiser) or the AMBI-PUR® fragrance diffuser (manufactured by Sara Lee). Generally, these devices consist of a perfume or fragrance source, an electrical heater, and a power supply. By the application of heat to the perfume or fragrance source, there will be a continuous supply of the perfume or fragrance to the space in which the device is placed.

The problem with this arrangement is that a person occupying the space will quickly become accustomed to the perfume or fragrance and, after a while, will not perceive the fragrance strength as being as intense, and may not notice it at all. This is a well-known phenomenon called habituation. A solution to this problem has been sought.

One effort to deal with this problem is described in U.S. Patent Application Publication No. US 2002/0159916 A1, to Whitby et al. The Whitby et al. patent application discloses a method and device adapted to provide to a space, two or more fragrance compositions, at least one of which fragrance compositions is provided periodically. The method and device may provide a continuous supply of a first fragrance composition and a periodic supply of a second fragrance composition. The fragrance composition(s) may be vaporized by heating and may include deodorant and/or insecticidal compounds. The fragrance compositions are preferably chosen such that the two fragrance compositions contrast with one another or have different notes. The fragrance composition is generally pulsed from a device which includes a heater. The periodic supply of heat to release the fragrance composition is controlled by providing the device, and particularly the heater, with a controller. The controller is in the form of an electronic circuit. The controller is arranged such that the heater runs for a short period of time, preferably from 15 seconds to 15 minutes with "appropriate intervals of time there between."

The Whitby et al. patent application, however, appears to be directed primarily to maintaining or sustaining the olfactory impact of the fragrance composition being emitted continuously, rather than to providing to the user noticeable changes in fragrances. In addition, although the Whitby et al. patent application mentions periodic supply of two or more fragrances, there is no specific teaching of emission patterns or programs dictating the supply of the different fragrances relative to each other so that the users actually experience distinct fragrances rather than one fragrance, which is a blend of the two compositions.

SUMMARY OF THE INVENTION

Features and Advantages of the Invention

The present inventors have discovered that the decrease in a user's scent perception is due to not only the well documented phenomenon of habituation, but also to physical, mechanical, and/or chemical changes that occur within the scent-emitting device during use. In particular, it has been found that during use, emissions from wicks diminish as a function of time, at least in part due to wick clogging. Wick clogging reduces volatilization (or evaporation), and hence the perception, of the perfume components. The clogging phenomenon can be caused by, for example, chemical reactions in the perfume composition, and gradual but selective evaporation of non-clogging perfume components. The present invention addresses these problems.

In some embodiments, the present invention provides a scent experience to a user that is more noticeable and constant over time, as compared to existing products. In some embodiments, the present invention reduces the adaptation/habituation effect by alternating perfumes. In other embodiments, the present invention provides a more efficient scent release profile of one or more perfumes. In yet other embodiments, the present invention reduces the adaptation/habituation effect and provides a more efficient perfume release profile. The present invention provides a longer lasting noticeable scent experience to a user.

Summary Of The Invention

The present invention relates to methods and devices for emitting volatile compositions that contain scent compositions, insecticides, malodor control compositions, and the like. In some embodiments, the invention relates to methods for emitting one or more volatile compositions. In some embodiments, the invention relates to methods and devices for emitting two or more volatile compositions. There are numerous embodiments of the methods and devices described herein, all of which are intended to be non-limiting examples.

In some embodiments of the method, it may be desirable for those who either experience the emission of a perfume composition(s), or who are in the presence of the device(s) emitting perfume composition(s), to experience and/or perceive a pleasant scent all of the time. In other cases, this may not be all of the time, but all of the time that such persons wish to perceive a scent. In some embodiments in which the method is used to emit two or more volatile perfume compositions, it may be desirable to maximize the perceptibility of each of two or more separate and distinct volatile perfume compositions. Thus, the method can do more than merely prevent habituation to a given emitted scent. In such embodiments, therefore, it may be desirable for the time for emission of the two or more volatile perfume compositions not to change too quickly; otherwise, there will not be a perception of the different scents, but rather a blended scent. In other embodiments, however, it may also be desirable to provide a blended scent experience, for at least a period of time.

In one embodiment of the method, the volatile compositions are alternately emitted during discrete emission periods that are greater than 15 minutes and less than or equal to 24 hours. The device can automatically switch to alternate the volatile composition being emitted. In other embodiments, the device may emit volatile compositions for periods less than or equal to 15 minutes; or it may emit volatile compositions for periods greater than 24 hours (e.g., 48 hours). Numerous other embodiments are possible.

The method can utilize one or more emission devices. In one embodiment that emits volatile perfume composition(s), a single device is used that is a dual scented electric diffuser that switches back and forth, or toggles, between two (or more) scents. In another embodiment that emits multiple volatile composition(s) such as perfume compositions and malodor control compositions, a single device is used that toggles between the compositions. In such embodiments, the emission device has a housing that is supported on an electrical outlet by a plug at least indirectly joined to the housing. The device contains a first volatile composition and a second volatile composition. The first volatile composition is emitted in an alternating period relative to said second volatile composition. Numerous other types of devices are possible. For example, in other embodiments, the method described herein can be carried out by two or more emission devices. Such dispensing devices comprise any type of emission device, including, but not limited to aerosol sprayers.

The present invention is also directed to methods improving the emission of volatile compositions from heated-wick devices that comprise at least one porous wick that is in fluid communication with a reservoir containing a volatile composition. In one embodiment, the method provides for flattening the perfume-release profile from a heated-wick perfume composition-dispensing device of a perfume composition having one or more components, comprising: a) applying heat to warm the wick to a temperature sufficient to increase the rate of volatilization of at least one component of the volatile perfume composition; b) reducing the heat to decrease the temperature of the wick sufficient to decrease the rate of volatilization of the at least one component of the perfume composition; c) maintaining the reduced heat for a time sufficient to allow for all or a portion of the components of the perfume composition to flow back through the wick toward the reservoir, or otherwise undergo diffusion to achieve equilibrium concentration within the wick ("back-flow"); and repeating a). The heat applied to a wick that is sufficient to increase the rate of volatilization of at least one component of the perfume composition can be a temperature from greater than 21° C. to about 80° C. or greater, so as to achieve a wick temperature from about 31° C. to about 80° C. or greater, or from about 40° C. to about 80° C., or from about 40° C. to about 60° C., or from about 60° C. to about 80° C. In one embodiment, the heat applied to the wick will increase the temperature of the wick over ambient in increments of approximately 10° C. The temperature that is sufficient to achieve a decrease the rate of volatilization of the at least one component of the perfume composition can be less than or equal to about 60° C., 40° C., or 20° C., or less. Preferably, the temperature of the wick is reduced by about 10° C. from the heated temperature, and more preferably the temperature of the wick is reduced to ambient temperature. In repeated heating steps, the heat applied to the wick can result in a wick temperature that is higher than in the previous heating step.

According to the inventive methods, the time sufficient to allow for back-flow of all or a portion of the components of the perfume composition can be from about 15 minutes to about 48 hours, or from about 17 minutes to about 72 minutes, or from about 20 minutes to about 60 minutes, or about 54 minutes, or about 30 minutes.

Some aspects of the inventive methods include repeating steps b) and c). In some instances, a), b), and c), are each repeated at least two, three, or four times; steps a), b), and c) may be repeated a hundred or more times.

In some embodiments of the invention, the heated-wick perfume composition-dispensing device comprises at least a first and second wick, each drawing, respectively, from at least a first and second perfume composition reservoir, and the method comprises: a1) applying heat to the first wick to increase volatilization of at least one component of the first perfume composition; b1) reducing the heat applied to the first wick to a temperature sufficient to decrease volatilization of the at least one component of the first perfume composition; c1) maintaining the reduced heat applied to the first wick for a time sufficient to allow for back-flow of all or a portion of the components of the first perfume composition; a2) applying heat to the second wick to increase volatilization of at least one component of the second perfume composition; b2) reducing the heat applied to the second wick to a temperature sufficient to decrease volatilization of the at least one component of the second perfume composition; c2) maintaining the reduced heat applied to the second wick for a time sufficient to allow for back-flow of all or a portion of the components of the second perfume composition; repeating a1); and repeating a2). In some embodiments, performance of a1) and a2) overlaps for at least about 0.1 seconds to about 15 minutes or more. In other embodiments, the performance of a1) and a2) does not overlap.

The invention also provides a scent-dispensing system comprising: a heated-wick perfume composition-dispensing device that is adapted to receive at least one perfume module, which comprises a reservoir containing a perfume composition, and a wick in fluid communication with the perfume composition, wherein the device, in use, applies heat to the wick to increase volatilization of at least one component of the perfume composition; reduces the applied heat to a temperature sufficient to decrease volatilization of the at least one component of the perfume composition; maintains the reduced heat for a time sufficient to allow for back-flow of all or a portion of the components of the perfume composition; and applies heat to the wick to increase volatilization of at least one component of the perfume composition. In some embodiments, the time sufficient to allow for back-flow is at least about 30 minutes.

In some embodiments of the inventive scent-dispensing system, the device, in use, automatically applies heat and automatically reduces heat. In some embodiments, the scent-dispensing device comprises a manually adjustable thermostat.

In some embodiments of the inventive scent-dispensing system comprises at least two compartments, each compartment or chamber being occupied respectively by each of at least two perfume compositions, and a cap that defines at least two vent holes, each vent hole positioned to cover each of said at least two compartments, said cap comprising a movable cover, which, in use, can be alternately positioned over one or more of each of said vent holes.

The invention also provides a method for dispensing fragrance to enhance perception of at least one perfume or other volatile composition using a scent-dispensing system comprising a cover, wherein the position of the cover is automatically moved in an alternating sequence. In some embodiments the position of the cover is automatically moved in a random alternating sequence. In some embodiments, the vent holes comprise slits or louvers or both.

The present invention also provides a perfume module for use with a heated-wick perfume composition-dispensing device, wherein the perfume module comprises at least one reservoir containing a perfume composition in fluid communication with a wick, wherein greater than about 70% of the at least one perfume composition's components have a gas chromatographic Kovats index (as determined on 5% Phenyl-methylpolysiloxane as non-polar silicone stationary phase) of less than about 1800. In some embodiments, greater than about 85%, greater than about 90%, greater than about 95%, greater than about 97%, or greater than about 99%, of the at least one perfume composition's components have a gas chromatographic Kovats index (as determined on 5% Phenyl-methylpolysiloxane as non-polar silicone stationary phase) of less than about 1800. In some embodiments, greater than about 85%, greater than about 90%, greater than about 95%, greater than about 97%, or greater than about 99%, of the at least one perfume composition's components have a gas chromatographic Kovats index (as determined on 5% Phenyl-methylpolysiloxane as non-polar silicone stationary phase) of less than about 1600. In some embodiments, greater than about 80% of the at least one perfume composition's components have a gas chromatographic Kovats index (as determined on 5% Phenyl-methylpolysiloxane as non-polar silicone stationary phase) of less than about 1600, or less than about 1500, or less than about 1400. In some embodiments, less than about 15%, less than about 10%, less than about 5%, or less than about 1% of the at least one perfume composition's components have a gas chromatographic Kovats index (as determined on 5% Phenyl-methylpolysiloxane as non-polar silicone stationary phase) of more than about 1600 and less than about 1800.

The inventive perfume modules can comprise one or two reservoirs. In embodiments comprising two or more reservoirs, each reservoir comprises a different perfume composition. The different perfume compositions can emit different scents or the same scents.

The wick can be made from any suitable material. For example, the wick included in the perfume module can be made from a material chosen from cellulose fibers, metal, plastic, ceramic, graphite, and cloth. In some embodiments, the wick is made from a plastic material chosen from high-density polyethylene (HDPE), polytetrafluoroethylene (PTFE), ultra-high molecular weight polyethelene (UHMW), nylon 6 (N6), polypropylene (PP), polyvinylidine fluoride (PVDF), and polyethersulfone (PES). Regardless of the material of manufacture, the wick can exhibit an average pore size of from about 10 microns to about 500 microns, or from about 50 microns to about 150 microns, or an average pore size of about 70 microns. The average pore volume of the wick is from about 15% to about 85%, or from about 25% to about 50%. Good results have been obtained with wicks having an average pore volume of about 38%. The wick can also be of variable length, such as, from about 1 mm to about 100 mm, or from about 5 mm to about 75 mm, or from about 10 mm to about 50 mm.

The present invention further provides fragrance-dispensing kits comprising: perfume modules in combination with heated-wick perfume composition-dispensing systems, wherein the perfume module and the heated-wick perfume composition-dispensing device are in operable communication. In some embodiments, these kits also include at least one refill perfume module that is not in operable communication with the heated-wick perfume composition-dispensing device.

The present invention is also directed to a scent-dispensing kit comprising: at least one perfume composition; and a heated-wick perfume composition-dispensing device that, in use, applies heat to the wick to increase the wick temperature and thereby increase volatilization of at least one component of the perfume composition; reduces the heat to a temperature sufficient to decrease volatilization of the at least one component; maintains the reduced heat for a time sufficient to allow for back-flow of all or a portion of the components of the perfume composition; and applies heat to the wick to increase volatilization of at least one component of the perfume composition. In some embodiments, the time to allow for back-flow during each cycle can be from at least 17 minutes to about 72 minutes.

In some embodiments of the scent-dispensing kits according to the invention, greater than about 70%, 75%, 80%, 85%, 90%, 95%, 97%, or 99% by weight, of the at least one perfume composition's components have a gas chromatographic Kovats index (as determined on 5% Phenyl-methylpolysiloxane as non-polar silicone stationary phase) of less than about 1800. In some embodiments, greater than about 90% or 95% by weight of the at least one perfume composition's components have a gas chromatographic Kovats index (as determined on 5% Phenyl-methylpolysiloxane as non-polar silicone stationary phase) of less than about 1600, 1500, or 1400.

In kits according to the invention, the heated-wick perfume composition-dispensing device can comprise at least two wicks and the kit can comprise at least two different perfume compositions. The different perfume compositions can exhibit different fragrances.

The invention is also directed to methods for increasing the perception of at least one fragrance dispensed from a heated-wick perfume composition-dispensing device, comprising: providing a device comprising at least first and second wicks in fluid communication with at least first and second separate perfume composition reservoirs, wherein the device dispenses fragrance by: a1) applying heat to the first wick to achieve a wick temperature sufficient to increase volatilization of at least one component of a first perfume composition; b1) reducing the heat applied to the first wick to achieve a wick temperature sufficient to decrease volatilization of the at least one component of the first perfume composition; c1) maintaining the reduced heat applied to the first wick for a time sufficient to allow for back-flow of all or a portion of the components of the first perfume composition; a2) applying heat to the second wick to achieve a wick temperature sufficient to increase volatilization of at least one component of a second perfume composition; b2) reducing the heat applied to the second wick to achieve a wick temperature sufficient to decrease volatilization of the at least one component of the second perfume composition; c2) maintaining the reduced heat applied to the second wick for a time sufficient to allow for back-flow of all or a portion of the components; repeating a1); and repeating a2).

In some methods according to the invention, the first and second perfume compositions are the same; in other embodiments, they are different. Different perfume compositions can exhibit different fragrances.

The present invention is also directed to methods for dispensing fragrance to enhance perception of at least one perfume, comprising: providing a device comprising at least first and second separate perfume composition-containing reservoirs, wherein the device dispenses fragrance by providing alternating bursts of emission of each of the at least first and second perfume compositions; and wherein the amount of perfume emitted per burst does not substantially vary.

In methods of the invention, the device can comprise at least first and second heaters and at least first and second wicks having a top end and a bottom end, each of the wicks in fluid communication at its bottom end with, respectively, each of the at least first and second separate perfume composition-containing reservoirs, and each of said wicks is in contact at its top end with, respectively, each the at least first and second heater, wherein the device dispenses fragrance by a1) applying heat to the first wick to achieve a wick temperature sufficient to increase volatilization of at least one component of a first perfume composition; b1) reducing the heat applied to the first wick to achieve a wick temperature sufficient to decrease volatilization of the at least one component of the first perfume composition; c1) maintaining the reduced heat applied to the first wick for a time sufficient to allow for back-flow of all or a portion of the components of the first perfume composition; a2) applying heat to the second wick to achieve a wick temperature sufficient to increase volatilization of at least one component of a second perfume composition; b2) reducing the heat applied to the second wick to achieve a wick temperature sufficient to decrease volatilization of the at least one component of the second perfume composition; c2) maintaining the reduced heat applied to the second wick for a time sufficient to allow for back-flow of all or a portion of the components of the second perfume composition; repeating a1); and repeating a2). The device can be designed to automatically cycle through heat application and heat reduction of each wick, wherein the time to allow for back-flow during each cycle is at least 15 minutes, and preferably 30 minutes, and more preferably 45 minutes.

The present invention is also directed to methods for reducing the decline in the rate, over a period of time, of perfume emission from a heated-wick perfume composition-dispensing device, comprising increasing the heat applied to the wick of the device, over the period of time, wherein the increased heat is sufficient to reduce the decline in the rate of perfume emission during the period of time.

The present invention is also directed to methods for achieving an approximately constant rate of emission of perfume, over a period of time, from a heated-wick perfume composition-dispensing device, comprising increasing the heat applied to the wick of the device, over the period of time, wherein the increased heat is sufficient to achieve a wick temperature to volatilize one or more components of the perfume composition which were not volatilized at the lower heat.

Still further, the invention provides scent-dispensing systems comprising: a heated-wick perfume composition-dispensing device that is adapted to receive at least one perfume module comprising a perfume reservoir containing a perfume composition, and a wick in fluid communication with the perfume composition, wherein the scent-dispensing device, in use, automatically cycles through application and withdrawal of heat to the wick; and wherein the scent-dispensing device automatically increases the heat applied to the wick at least one time after a set time interval. The set time interval can be from about 7 to about 30 days, or from about 7 to about 15 days. The heat applied to the wick can be increased two or more times.

The invention is also directed to heated-wick perfume composition-dispensing devices containing at least one perfume composition, wherein greater than about 95% of the at least one perfume composition's components have a gas chromatographic Kovats index (as determined on 5% Phenyl-methylpolysiloxane as non-polar silicone stationary phase) of less than about 1800. The devices of the invention can include a wick, which can be made from a number of materials, including materials chosen from cellulose fibers, metal, plastic, ceramic, graphite, and cloth. Plastic materials include, but are not limited to, high-density polyethylene (HDPE), polytetrafluoroethylene (PTFE), ultra-high molecular weight polyethelene (UHMW), nylon 6 (N6), polypropylene (PP), polyvinylidine fluoride (PVDF), and polyethersulfone (PES). Porous wicks can exhibit an average pore size of from about 10 microns to about 500 microns, or from about 50 microns to about 150 microns. The average pore volume can range from about 15% to about 75%, or from about 25% to about 50%, or about 38%. The length of the wick can range from about 1 mm to about 100 mm, or from about 5 mm to about 75 mm, or from about 10 mm to about 50 mm.

Perfume compositions according to this invention can comprise components chosen from a variety of ingredients such as those listed in Tables 1-9.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention, and together with the description, serve to explain the principles of the invention.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE INVENTION

Figure 1:
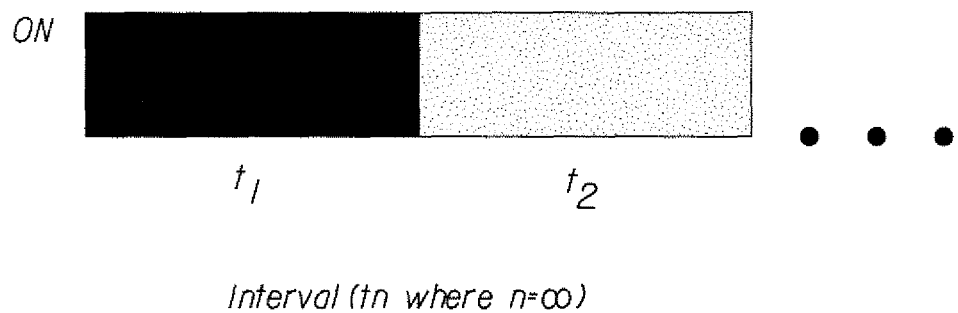
FIG. 1 is a diagram that shows one non-limiting embodiment of an emission program for emitting two volatile compositions.

Reference will now be made in detail to the present embodiments (exemplary embodiments) of the invention, examples of which are illustrated in the accompanying drawings. Wherever possible, the same reference numbers will be used throughout the drawings to refer to the same or like parts.

The present invention relates to methods, devices, and systems for emitting volatile compositions, and additionally, to novel compositions. In some embodiments, the invention relates to methods and devices for emitting two or more volatile compositions. In some embodiments, the invention relates to emitting one or more volatile compositions. There are numerous embodiments of the methods and devices described herein, all of which are intended to be non-limiting examples.

The methods for emitting volatile compositions can comprise a variety of different embodiments. The volatile compositions can be fragrance compositions, compositions that function as insecticides, air fresheners, deodorants, aromacology, aromatherapy, insecticides, or any other material that acts to condition, modify, or otherwise charge the atmosphere or to modify the environment. The volatile materials emitted in a given embodiment of the method can be the same type of material (e.g., two or more fragrance compositions), or they can be different types of materials (e.g., fragrance compositions and air fresheners). Deodorants or malodor control compositions may comprise a material chosen from: odor neutralizing materials, odor blocking materials, odor masking materials, and combinations thereof. The methods can emit the volatile compositions in a sequence in which the emission of the different volatile compositions automatically alternates between the different volatile compositions.

The compositions can include components that are suitably used in volatile composition-emitting devices. The components are not limited, but can be selected based on their Kovats index ("KI;" as determined on 5% Phenyl-methylpolysiloxane as non-polar silicone stationary phase). Kovat's Index places the volatility attributes of an analyte (e.g., component of a volatile composition) on a column in relation to the volatility characteristics of n-alkane series on that column. Typical columns used are DB-5 and DB-1. By this definition, the KI of a normal alkane is set to 100n, wherein n=the number of C atoms of the n-alkane. The KI of an analyte, x, eluting at time t', between two n-alkanes with number of carbon atoms "n" and "N" having corrected retention times $t'_n$ and $t'_N$, respectively, will then be calculated as:

$$KI = 100\left(n + \frac{\log t'_x - \log t'_n}{\log t'_N - \log t'_n}\right) \quad (1)$$

On a non-polar to slightly polar GC stationary phase, KI of analytes are correlated with their relative volatility. For example, analytes with smaller KIs tend to be more volatile than those with larger KIs. Ranking analytes with their corresponding KI values gives a good comparison of analyte evaporation rates in liquid-gas partitioning systems. The volatile components according to the present invention can have a KI of less than or equal to about 1800, 1750, 1700, 1650, 1600, 1550, 1500, 1450, 1400, 1350, 1300, 1250, 1200, 1150, 1100, 1050, 1000, or less. The composition can comprise greater than or equal to about 70%, 80%, 90%, 91%, 92%, 93%, 94%, 95%, 96%, 97%, 98%, 99%, or even higher percent, by weight of said components having defined KIs.

The emission of volatile compositions can be controlled and optimized by adjusting wick temperature. Evaporation rate is related to wick temperature. This can be described using gas-liquid partition coefficient as defined below:

$$K = \frac{C_{li}}{C_{gi}} \quad (2)$$

Where $C_{li}$ is liquid phase concentration of analyte i, and $C_{gi}$ is the gas phase concentration of analyte i. K can then be described as follows:

$$\ln K = \frac{\Delta G^0}{RT_c} \quad (3)$$

Accordingly, increasing temperature will decrease the GC retention of an analyte. To adjust wick heating to accommodate volatile compositions within a range of KIs, heat is applied to a wick to result in an increase of 10° C. in wick temperature for an increase in KI of 100 KI units.

In some embodiments, volatile compositions for use at wick temperatures of about 60° C. comprise components wherein about 80% by weight of the components have a KI of less than about 1600, about 15% by weight of the components have a KI of greater than 1600 and less than 1800, and less than 5% by weight of the components have a KI of greater than 1800. An example of such an embodiment is a floral perfume composition as shown in Table 2, wherein 80.5% by weight of the components have a KI of less than about 1600, 15.0% by weight of the components have a KI of greater than 1600 and less than 1800, and 4.5% by weight of the components have a KI of greater than 1800. Another example is a floral perfume composition as shown in Table 3, wherein 81.5% by weight of the components have a KI of less than about 1600, 14.5% by weight of the components have a KI of greater than 1600 and less than 1800, and 4.0% by weight of the components have a KI of greater than 1800. Another example is a fruity perfume composition as shown in Table 5, wherein 82.5% by weight of the components have a KI of less than about 1600, 14.0% by weight of the components have a KI of greater than 1600 and less than 1800, and 3.5% by weight of the components have a KI of greater than 1800.

Another example is a fruity perfume composition as shown in Table 6, wherein 80.0% by weight of the components have a KI of less than about 1600, 17.0% by weight of the components have a KI of greater than 1600 and less than 1800, and 3.0% by weight of the components have a KI of greater than 1800. Another example is a outdoors perfume composition as shown in Table 8, wherein 80.5% by weight of the components have a KI of less than about 1600, 15.0% by weight of the components have a KI of greater than 1600 and less than 1800, and 4.5% by weight of the components have a KI of greater than 1800. Another example is a outdoors perfume composition as shown in Table 9, wherein 82.8% by weight of the components have a KI of less than about 1600, 13.2% by weight of the components have a KI of greater than 1600 and less than 1800, and 4.0% by weight of the components have a KI of greater than 1800. Another example is a gourmande perfume composition as shown in Table 1, wherein 84.0% by weight of the components have a KI of less than about 1600, 13.0% by weight of the components have a KI of greater than 1600 and less than 1800, and 3.0% by weight of the components have a KI of greater than 1800.

In some embodiments, volatile compositions for use at wick temperatures of about 40° C. comprise components wherein about 80% by weight of the components have a KI of less than about 1400, about 15% by weight of the components have a KI of greater than 1400 and less than 1600, and less than 5% by weight of the components have a KI of greater than 1600. An example of such an embodiment is a fruity perfume composition as shown in Table 7, wherein 80.9% by weight of the components have a KI of less than about 1400, 14.6% by weight of the components have a KI of greater than 1400 and less than 1600, and 4.5% by weight of the components have a KI of greater than 1600.

In some embodiments, volatile compositions for use at wick temperatures of about 80° C. comprise components wherein about 80% by weight of the components have a KI of less than about 1800, about 15% by weight of the components have a KI of greater than 1800 and less than 2000, and less than 5% by weight of the components have a KI of greater than 2000. An example of such an embodiment is a floral perfume composition as shown in Table 4, wherein 80.0% by weight of the components have a KI of less than about 1800, 17.0% by weight of the components have a KI of greater than 1800 and less than 2000, and 3% by weight of the components have a KI of greater than 2000.

TABLE 1

| Gourmande | | |
|---|---|---|
| Material | Percent | Kovats |
| Vanillin | 3.00 | 1413 |
| Coumarin | 1.00 | 1466 |
| Ethyl Maltol | 1.50 | 1207 |
| Ethyl Vanillin | 2.00 | 1474 |
| Methyl Anthranilate | 2.00 | 1359 |
| Anethole | 0.50 | 1299 |
| Dipropylene Glycol | 52.90 | 1044 |
| Para Hydroxy Phenyl Butanone | 0.80 | 1559 |
| Ethyl Methyl Phenyl Glycidate | 1.00 | 1496 |
| Iso Amyl Acetate | 1.00 | 877 |
| Benzaldehyde | 0.30 | 967 |
| Anisyl Acetate | 8.00 | 1429 |
| Cyclo Galbanate | 1.00 | 1430 |
| Cinnamyl Acetate | 2.00 | 1456 |
| Methyl Octalactone | 1.00 | 1322 |
| Methyl Cinnamate | 3.00 | 1398 |
| Gamma Nonalactone | 3.00 | 1375 |
| Galaxolide | 3.00 | 1893 |

TABLE 1-continued

| Gourmande | | |
|---|---|---|
| Material | Percent | Kovats |
| Cis 3 Hexenyl Salicylate | 9.00 | 1690 |
| Methyl Dihydro Jasmonate | 4.00 | 1665 |

TABLE 2

| Floral 1 | | |
|---|---|---|
| Material | Percent | Kovats |
| Citronellol | 15.00 | 1228 |
| Phenyl Ethyl Alcohol | 15.00 | 1122 |
| Phenyl Ethyl Acetate | 5.00 | 1265 |
| Phenyl Ethyl Phenyl Acetate | 1.00 | 1945 |
| Rose Oxide | 0.30 | 1129 |
| Lyral | 10.00 | 1680 |
| Geraniol | 5.00 | 1258 |
| Linalool | 7.00 | 1102 |
| Cis 3 Hexenyl Salicylate | 5.00 | 1690 |
| Ligustral | 1.00 | 1105 |
| Nerol | 8.80 | 1233 |
| Geranyl Nitrile | 3.00 | 1249 |
| Iso Cyclo Geraniol | 3.00 | 1236 |
| Iso Eugenol | 0.50 | 1464 |
| Citronellyl Oxy Acetaldehyde | 0.30 | 1414 |
| Alpha Damascone | 0.30 | 1412 |
| Ionone Gamma Methyl | 5.00 | 1500 |
| Ethylene Brassylate | 1.00 | 2060 |
| Cinnamic Alcohol | 1.00 | 1316 |
| Sandalore | 8.00 | 1512 |
| Coumarin | 2.00 | 1466 |
| Ionone Beta | 0.30 | 1507 |
| Galaxolide | 2.5 | 1893 |

TABLE 3

| Floral 2 | | |
|---|---|---|
| Material | Percent | Kovats |
| Alpha Damascone | 0.30 | 1412 |
| Iso Pulegol | 1.50 | 1172 |
| Lacto Jasmone | 1.50 | 1482 |
| Indolarome | 0.20 | 1499 |
| Vanillin | 1.00 | 1413 |
| Amyl Salicylate | 15.00 | 1578 |
| Ebanol | 2.00 | 1464 |
| Iso Eugenol | 0.50 | 1464 |
| Methyl Anthranilate | 0.50 | 1359 |
| Lyral | 5.00 | 1680 |
| Methyl Dihydro Jasmonate | 9.00 | 1665 |
| Cinnamic Alcohol | 2.00 | 1316 |
| Phenyl Ethyl Alcohol | 15.00 | 1122 |
| Linalool | 12.70 | 1102 |
| Methyl Benzoate | 1.00 | 1104 |
| Benzyl Acetate | 5.00 | 1169 |
| Cinnamic Aldehyde | 20.00 | 1288 |
| Eugenol | 0.30 | 1369 |
| Ionone Gamma Methyl | 3.00 | 1500 |
| Galaxolide | 3.00 | 1893 |
| Ethylene Brassylate | 1.00 | 2060 |
| Ambrox | 0.50 | 1798 |

TABLE 4

Floral 3

| Material | Percent | Kovats |
| --- | --- | --- |
| Phenyl Ethyl Alcohol | 15.00 | 1122 |
| Citronellol | 10.00 | 1228 |
| Geraniol | 5.00 | 1258 |
| Benzyl Acetate | 10.00 | 1169 |
| Methyl Dihydro Jasmonate | 10.00 | 1665 |
| Hexyl Cinnamic Alcohol | 11.70 | 1770 |
| P. T. Bucinal | 5.00 | 1517 |
| Alpha Damascone | 0.30 | 1412 |
| Rose Oxide | 0.20 | 1148 |
| Coumarin | 3.00 | 1466 |
| Ethylene Brassylate | 3.00 | 2060 |
| Habanolide | 5.00 | 1860 |
| Galaxolide | 5.00 | 1893 |
| Sandalore | 5.00 | 1512 |
| Ionone Gamma Methyl | 3.00 | 1500 |
| Methyl Cedrylone | 2.00 | 1813 |
| Cinnamic Alcohol | 1.00 | 1316 |
| Ambrox | 0.50 | 1798 |
| Tonalid | 5.00 | 1902 |
| Iso Eugenol | 0.30 | 1464 |

TABLE 5

Fruity 1

| Material | Percent | Kovat |
| --- | --- | --- |
| Ethyl-2-Methyl Butyrate | 2.00 | 850 |
| Verdox | 30.00 | 1313 |
| Dihydro Myrcenol | 17.50 | 1072 |
| Mayol | 20.00 | 1289 |
| Hexyl Acetate | 5.00 | 1011 |
| Prenyl Acetate | 3.00 | 918 |
| Ligustral | 1.00 | 1105 |
| Ethylene Brassylate | 0.50 | 2060 |
| Gamma Nonalactone | 3.00 | 1375 |
| Habanolide | 3.00 | 1860 |
| Ethyl Aceto Acetate | 1.00 | 941 |
| Hexyl Salicylate | 3.00 | 1713 |
| Methyl Dihydro Jasmonate | 6.00 | 1665 |
| Lyral | 5.00 | 1680 |

TABLE 6

Fruity 2

| Material | Percent | Kovats |
| --- | --- | --- |
| Allyl Heptoate | 2.00 | 1180 |
| Allyl Caproate | 2.00 | 1079 |
| Allyl Amyl Glycolate | 3.00 | 1237 |
| Benzyl Acetate | 15.00 | 1169 |
| Damascenone | 0.30 | 1403 |
| Ethyl-2-Methyl Butyrate | 1.50 | 850 |
| Ethyl Maltol | 1.00 | 1207 |
| Phenoxy Ethyl Isobutyrate | 2.00 | 1528 |
| Linalool | 12.30 | 1102 |
| Methyl Dihydro Jasmonate trans | 5.00 | 1665 |
| Cis 3 hexenyl Salicylate | 12.00 | 1690 |
| Rose Oxide | 0.20 | 1129 |
| Verdox | 15.00 | 1313 |
| Iso Amyl Acetate | 0.50 | 877 |
| Benzaldehyde | 0.20 | 967 |
| Dihydro Myrcenol | 20.00 | 1072 |
| Linalyl Acetate | 5.00 | 1257 |
| Habanolide | 3.00 | 1860 |

TABLE 7

Fruity 3

| Material | Percent | Kovats |
| --- | --- | --- |
| Ethyl-2-Methyl Butyrate | 1.50 | 850 |
| Prenyl Acetate | 2.00 | 918 |
| Ligustral | 1.00 | 1105 |
| Iso Amyl Acetate | 0.50 | 877 |
| Allyl Caproate | 2.00 | 1079 |
| Allyl Amyl Glycolate | 3.00 | 1237 |
| Hexyl Acetate | 5.00 | 1011 |
| Melonal | 1.00 | 1045 |
| Benzyl Acetate | 15.00 | 1169 |
| Dihydro Myrcenol | 29.90 | 1072 |
| Alpha Damascone | 0.30 | 1412 |
| Cis 3 Hexenyl Salicylate | 3.00 | 1690 |
| Verdox | 20.00 | 1313 |
| Ionone Gamma Methyl | 4.00 | 1500 |
| Sandalore | 4.00 | 1512 |
| Neobutanone | 0.30 | 1476 |
| Para Hydroxy Phenyl Butanone | 1.00 | 1559 |
| Ethyl Methyl Phenyl Glycidate | 2.00 | 1496 |
| Florhydral | 3.00 | 1445 |
| Galaxolide | 1.50 | 1893 |

TABLE 8

Outdoors 1

| Material | Percent | Kovats |
| --- | --- | --- |
| Undecavertol | 2.00 | 1269 |
| Melonal | 1.00 | 1045 |
| Ligustral | 1.00 | 1105 |
| Hexyl Cinnamic Alcohol | 2.00 | 1770 |
| Methyl Dihydro Jasmonate | 4.00 | 1665 |
| Benzyl Acetate | 20.00 | 1169 |
| Helional | 5.00 | 1589 |
| Floralozone | 2.00 | 1459 |
| Cis 3 Hexenyl Salicylate | 3.00 | 1690 |
| Lyral | 6.00 | 1680 |
| Habanolide | 2.50 | 1860 |
| Calone 1951 | 0.30 | 1429 |
| Galaxolide | 2.00 | 1893 |
| Dihydro Myrcenol | 20.00 | 1072 |
| Citronellol | 20.00 | 1228 |
| Phenyl Ethyl Alcohol | 9.20 | 1122 |

TABLE 9

Outdoors 2

| Material | Percent | Kovats |
| --- | --- | --- |
| Linalyl Acetate | 7.00 | 1257 |
| Methyl Cedrylone | 1.00 | 1813 |
| Habanolide | 3.00 | 1860 |
| Sandalore | 8.00 | 1512 |
| Ionone Gamma Methyl | 5.00 | 1500 |
| Methyl Dihydro Jasmonate | 5.00 | 1665 |
| Iso Menthone | 1.00 | 1182 |
| Linalool Oxide | 1.00 | 1088 |
| Dihydro Myrcenol | 41.50 | 1072 |
| Alpha Damascone | 0.30 | 1412 |
| Ligustral | 0.80 | 1105 |
| Neobutanone | 0.20 | 1448 |
| Ambrox | 0.20 | 1798 |
| Violiff | 2.00 | 1375 |
| Cymal | 1.00 | 1477 |
| Hexyl Salicylate | 8.00 | 1713 |
| Benzyl Acetate | 15.00 | 1169 |

In some embodiments, a volatile composition is emitted from a single source for a period, which is then followed by a period of decreased emission. Thus, the invention contemplates alternating, or toggling, between "on" and "off" emission of a volatile composition.

The period of emission can range from as little as about 15 minutes to as long as about 48 hours. Intermediate periods of emission can be 20, 25, 30, 35, 40, 45, 50, 55, and 60 minutes, and 2, 3, 4, 5, 6, 12, 18, and 24 hours, and any other intermediate time. Of course, the period of emission can range from any recited time to any recited time, for example, from 20 minutes to 24 hours, or from 30 minutes to one hour. One particular example of an emission period is 30 minutes. Another example is 45 minutes.

The period of decreased emission is similarly variable. It can range from as little as about 15 minutes to as long as about 48 hours. Intermediate periods of decreased emission can be 20, 25, 30, 35, 40, 45, 50, 55, and 60 minutes, and 2, 3, 4, 5, 6, 12, 18, and 24 hours, and any other intermediate time. Of course, the period of decreased emission can range from any recited time to any recited time, for example, from 20 minutes to 24 hours, or from 30 minutes to one hour. One particular example of a decreased emission period is 30 minutes. Another example is 45 minutes.

Decreased emission can be characterized by any decrease in emission. The decrease in emission can be measured quantitatively, e.g., by a decrease in the weight (mg) of a volatile composition delivered into a surrounding environment per unit time, or it can be measured qualitatively, e.g., by user perception. The decrease can be small or large, and can result in minimal or no emission. That is, emission can be reduced to its ambient level, i.e., the level of emission that occurs in the absence of deliberately applied external energy (e.g., electricity in the form of heat) added to the system; a common ambient temperature for an internal environment is in the range of from about 65° F. to about 75° F. (18° C. to about 24° C.).

The present invention contemplates that two or more volatile compositions can be emitted. The two or more compositions can be the same, or they can be different. Different compositions may be designed to exhibit the same or different properties, such as the same fragrance or a different fragrance, or a fragrance and a malodor control.

Emission of the two or more volatile compositions can be performed such that the two or more compositions are emitted at the same or different times. Thus, in some embodiments, emission of the two or more compositions can entirely overlap. On the other hand, emission can be designed such that there is no overlap at all. And emission can also be designed such that there is from very small overlap in emission time to very large overlap in emission time. For example, overlap in emission time can be as little as 0.1 seconds to as much as 48 hours. Emission can be designed so that when one composition is emitted, a second is not being emitted; and when a second composition is being emitted, a first is not being emitted. Thus, the invention contemplates alternating, or toggled, emission of two or more compositions.

As noted above, emission of a volatile composition can occur for a period of as little as, for example, 15 minutes, to as long as, for example, 48 hours. The emission can be any time in between, and in some embodiments, volatile composition emission is 30 minutes. In other embodiments, volatile composition emission is 45 minutes. Where two or more compositions are emitted, a first composition can be delivered for 30 minutes ("ON"), during which time a second composition is not delivered ("OFF"). During the following 30 minutes, the first composition is OFF and the second is ON. Of course, there can be ramping toward ON and/or OFF, such that during the ramping phase, there is some overlap in emission of the compositions.

Of course, two or more volatile compositions can be emitted in any suitable sequence. The sequence of emission of the volatile compositions can be in a pattern, or it can be random. The term "pattern," as used herein, refers to repeating sequences. In embodiments where the sequence of emission of the different volatile compositions is repeatable, the pattern can be repeated once, or any number of times after the initial sequence. The term "random," as used herein, refers to sequences in which the sequence of emission of the volatile compositions does not repeat in a regular fashion. It is also possible for an emission sequence to comprise a portion of time where the sequence is in a pattern, and a portion of time in which the sequence is random.

Figure 2:
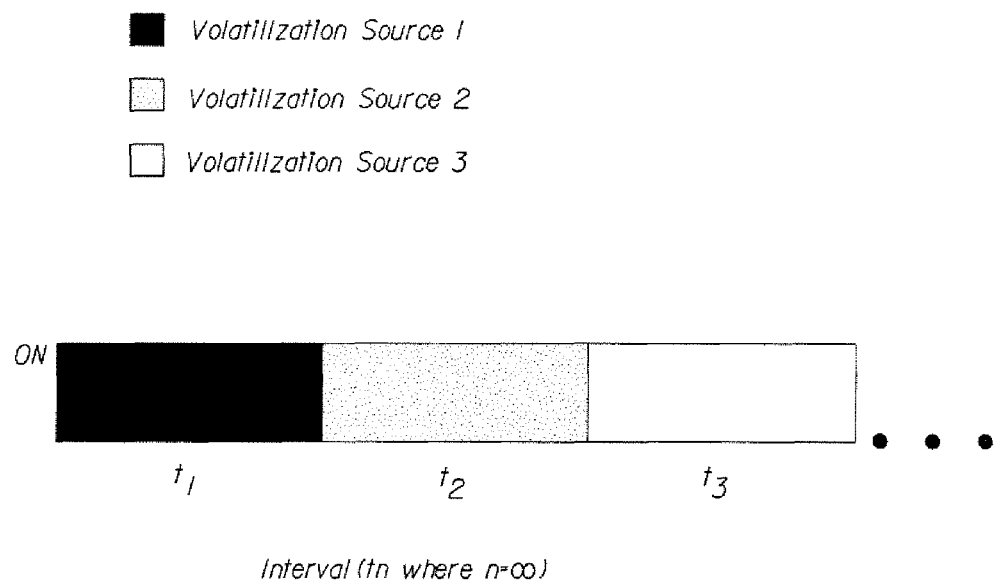
FIG. 2 is a diagram that shows one non-limiting embodiment of an emission program for emitting three (or more) volatile compositions.

In some embodiments, two or more volatile compositions are emitted in an alternating sequence. For example, there can be a first volatile composition and a second volatile composition, and the first volatile composition is emitted in an alternating period relative to said second volatile composition. Thus, if the first volatile composition is designated "1," and the second volatile composition is designated "2," the volatile compositions can be emitted in an alternating pattern as follows: 1, 2, 1, 2, . . . , etc. FIG. 1 shows such an emission program schematically. In FIG. 1, the diagram represents the periods during which the volatile compositions are being subjected to a source of energy (or "activated") (for example, if they are in a device which has a heater that heats the compositions, the diagram can designate the periods of time that during which the heaters are on and off). If there are three volatile compositions, they can be emitted in an alternating pattern as follows: 1, 2, 3, 1, 2, 3, . . . , etc. as shown in FIG. 2.

In viewing these Figures (and the diagrams which follow), it should be understood that these are non-limiting embodiments. In other embodiments, there need not be a separate volatilization source (such as a heater) for each volatile composition. There can be any suitable number of volatilization sources for the volatile compositions. For example, a single volatilization source can be used to volatilize more than one volatile composition. Such a volatilization source could, for example, be capable of moving to volatilize the different volatile compositions, or it can be capable of selectively directing energy (e.g., heat) to the different volatile compositions (such as by opening and closing a door or gate between the volatilization source and a given volatile composition). Alternatively, reservoirs can be movable relative to the volatilization source (so that the reservoirs can be selectively moved over a heater, for example).

The term "interval," as used herein, refers to the shortest period of time in the emission sequence. The term "discrete emission period," as used herein, refers to the individual time period that a given volatile material (or combination of volatile materials) is emitted in the emission sequence. This may correspond generally to the period of time that a heater, for example, is turned on for a given volatile material or combination of volatile materials (though there may be a slight lag between the operation of a heater and the emission of a volatile material). The discrete emission periods can also be referred to herein as a first time period, a second time period, etc. (each of which has a beginning and end). The term "burst" as used herein refers to an initial and peak release of a volatile composition after a heated wick is maintained at a reduced temperature to permit back flow of at least one of the components of the volatile composition. It should be understood that it is not necessary that the different volatile compositions be emitted for equal time periods. For example, after one volatile composition is emitted, a different volatile composition can be emitted for a shorter, or alternatively, a longer time period. In another example, after one volatile composition is emitted, it can be followed by another interval of the same volatile composition before a different volatile composition is emitted. In cases where the different volatile compositions are not emitted for equal time periods, it may be desirable to provide a greater amount of the compositions that are emitted for a longer cumulative time period so that the volatile compositions will be depleted at about the same time. There are numerous possible alternating emission sequences. In the case of three volatile compositions, non-limiting examples of some other possible patterns of emission include, but are not limited to: (1, 2 2, 1, 3 3); (1, 2, 3, 3, 2, 1); and (1, 2 2 2 2, 1 1, 3 3 3 3, 1).

In some embodiments of the method, the volatile compositions can be emitted during a discrete emission period that is less than or equal to about 15 minutes, but it may be more desirable for each emission period to be longer than 15 minutes. In the case of scented materials, longer time periods may be more desirable. In one embodiment of the method, the volatile compositions are alternately emitted during discrete periods that are each greater than 15 minutes and less than or equal to about 12 hours, or less than or equal to about 24 hours, or less than or equal to about 48 hours, or more. Every numerical range given throughout this specification will include every narrower numerical range that falls within such broader numerical range, as if such narrower numerical ranges were all expressly written herein. Thus, in another non-limiting embodiment, the volatile compositions are alternately emitted during periods that are greater than 15 minutes, or greater than or equal to about 1 hour, and less than 2 hours. In one embodiment, each volatile composition is emitted for a period of about 72 minutes. In one embodiment, each volatile composition is emitted for about 30 minutes.

Figure 3:
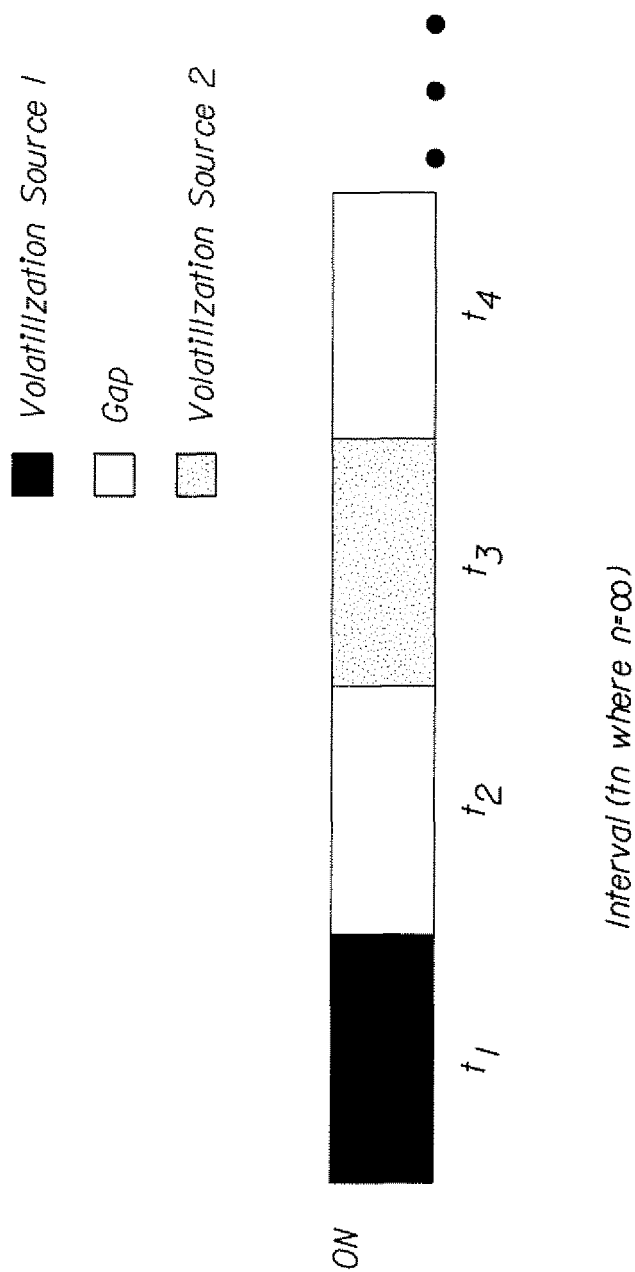
FIG. 3 is a diagram that shows one non-limiting embodiment of an emission program for emitting two (or more) volatile compositions where there is a gap between the emissions of the volatile compositions.
Figure 4:
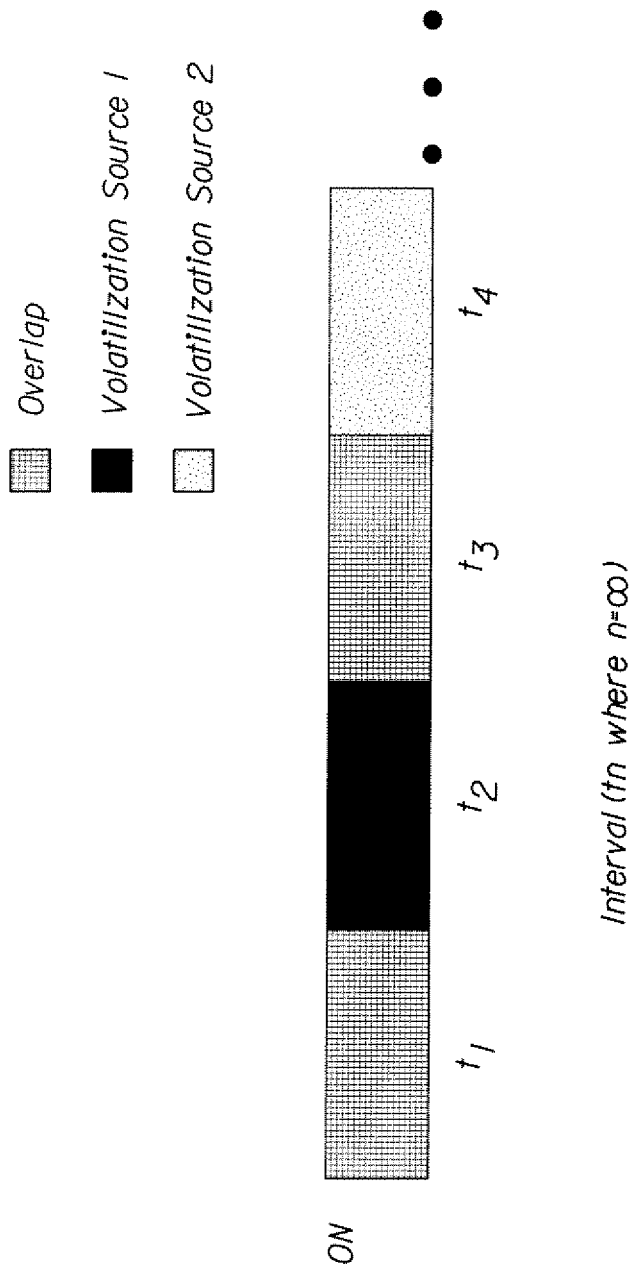
FIG. 4 is a diagram that shows one non-limiting embodiment of an emission program for emitting two (or more) volatile compositions where there is an overlap of the emissions of the volatile compositions.
Figure 5:
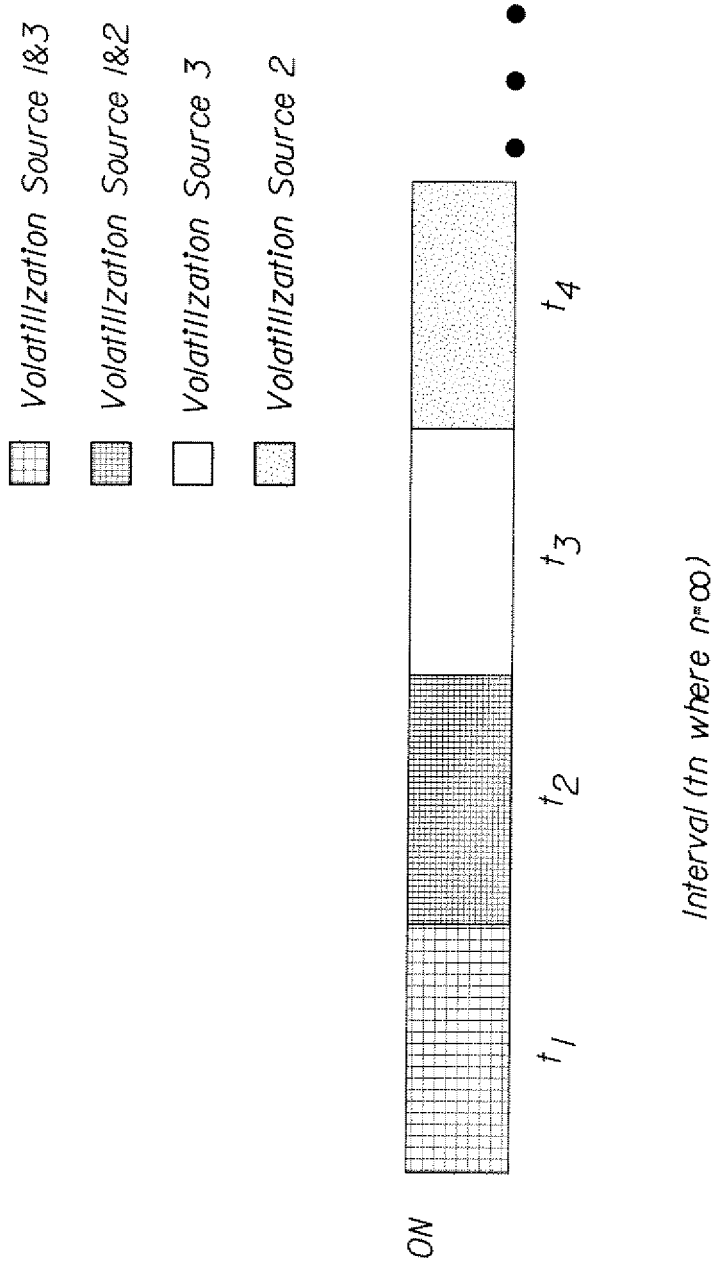
FIG. 5 is a diagram that shows one non-limiting embodiment of an emission program for emitting three (or more) volatile compositions where there is an overlap of the emissions of one volatile composition with the emission of two other volatile compositions.

The volatile compositions may be emitted so that one immediately follows the end of the emission period of the other. In other embodiments, the volatile compositions can be emitted so that there is a gap between the end of the emission period of one of the volatile compositions, and the beginning of the emission period of another volatile composition. FIG. 3 is a diagram that shows one non-limiting embodiment of an emission program for emitting two volatile compositions where there is a gap between the emissions of the volatile compositions where "g" designates a gap. In other embodiments, the volatile compositions can be emitted so that there is an overlap in the emission periods of two, or more volatile compositions. FIG. 4 is a diagram that shows one non-limiting embodiment of an emission program for emitting two volatile compositions where there is an overlap of the emissions of the volatile compositions where the symbol "&" designates an emission period where both volatile compositions are being emitted. FIG. 5 shows one non-limiting embodiment of an emission program for emitting three (or more) volatile compositions where there is an overlap of the emissions of one volatile composition with the emission of two other volatile compositions. In other embodiments, it is possible for one or more of the volatile compositions to be emitted continuously, and another volatile composition to be emitted for periods of time that are greater than 15 minutes.

If it is desirable to have a gap between the end of the emission period of one of the volatile materials, and the beginning of the emission period of another volatile material, the gap can be of any suitable duration. The gap period of between emissions of volatile material may be from greater than 0% up to 100% or more of the duration of either the previous or subsequent emission periods. If it is desirable to have an overlap in the emission periods of two, or more volatile materials, the overlap can be of any suitable duration.

The emission period of a subsequently emitted volatile material may overlap from greater than 0% up to 100% of the time a first volatile material is being emitted. In certain embodiments, for example, it may be desirable for there to be an overlap of about 25% between different volatile materials. For instance, instead of scent "A" being emitted for 60 minutes, followed by scent "B" being emitted for 60 minutes: scent "A" can be emitted for 45 minutes; this can be followed by the emission of both scents "A" and "B" for 30 minutes; and this followed by scent "B" for 45 minutes. In this case, 30 minutes is 25% of the total time of the emission of scents "A" and "B" and the combination thereof (or 120 minutes).

The gap or overlap periods can be controlled automatically. In certain embodiments of the article(s) or device(s) used to emit the volatile materials, the article(s) or device(s) can be provided with controls to allow the user to control the duration of any gap and/or overlap in emission periods. Overlapping sequences may be used for any purpose, such as, for example, when it is desirable to have the user smell the blended scent for some period as well as distinct scents during other periods.

In certain embodiments, it is desirable for the method to be carried out by article(s) and/or device(s) that are flameless (e.g., not candles). In certain embodiments, it may be desirable for the method to be carried out independently of other media (such other media may include, but is not limited to: movies, television, etc.). In other embodiments, it may be desirable to carry out the method in a coordinated fashion with other media.

There can be any suitable emission program or scheme for emitting the volatile compositions. In certain embodiments where scented materials are being emitted, it is desirable for the device to provide an alternating scent experience, rather than a sustained impression of a single scent. In one embodiment, it may be desirable to provide a day/night emission program where one scent is provided for waking a person, and another scent is provided for the period of time during which they are trying to go to sleep. Thus, in some embodiments, it may be desirable to deliver the same scent at the same time every day. In other embodiments, it may be desirable to avoid a routine scent experience. For example, it may be desirable for the emission pattern to not be synchronized over a 24-hour period, so that the user has a different scent experience at a given time during the day or night for each 24-hour period. Numerous other embodiments are possible.

The total emission program (or simply "the emission program") refers to the entire sequence of the discrete emission periods from beginning to end. In certain embodiments, it is desirable for the emission program to be continuous. The term "continuous," as used in reference to the emission program, means that there is a planned emission sequence over an entire period, once the program is initiated. This emission program can include periods, as noted above, where there are gaps in emission. This will still be considered to be a continuous emission program, although there will not necessarily be continuous emission of volatile compositions. It should be understood, however, that it is possible for the emission program to be interruptible by the user (e.g., turned off), if desired. Thus, the method can provide a user interface, and the user interface can provide a user with the ability to interrupt the emission program. In certain embodiments, the emission program may be designed to run continuously or substantially continuously until at least one of the volatile compositions is substantially depleted. In certain embodiments, it is desirable for the emission program to run continuously until all of the volatile compositions are substantially depleted, and for this to occur at approximately the same time.

The emission program can be of any suitable length, including but not limited to 30 days, 60 days, or shorter or longer periods, or any period between 30 to 60 days.

One example of a device that can be used in accordance with this invention is one that includes a wick. When used in such devices, the wick acts as a conduit to carry a volatile composition from a reservoir to a point of emission. A wick is generally porous, or includes pores, that provide for the flow of the volatile composition. Wicks can be made from a variety of materials, including but not limited to, cellulose fibers, metal, plastic, ceramic, graphite, and cloth. Synthetic materials, such as plastic, may be desirable because of their uniformity in performance. Plastic materials that can be used to form porous wicks include, but are not limited to, high-density polyethylene (HDPE), polytetrafluoroethylene (PTFE), ultra-high molecular weight polyethylene (UHMW), nylon 6 (N6), polypropylene (PP), polyvinylidine fluoride (PVDF), and polyethersulfone (PES).

Wicks can be described in terms of their average pore size. The wicks may have any suitable pore size. US Patent Application 2002/0136886 A1, titled "Porous Wick for Liquid Vaporizers" provides a description of standard measurement of pore size. In certain embodiments, the average pore size of wicks useful in the present invention ranges from about 10 microns to about 500 microns, or from about 50 microns to about 150 microns, or from about 60 to about 100, or about 70 microns. Wicks can have an average pore volume from about 15% to about 85%, or from about 25% to about 50%. Similarly, wicks can vary in length, depending solely on the desired use. In certain embodiments, wicks can be as short as 1 mm or as long as 100 mm, or longer, or any length in between. Wicks can range in length from about 5 mm to about 75 mm, or from about 10 mm to about 50 mm.

Figure 6:
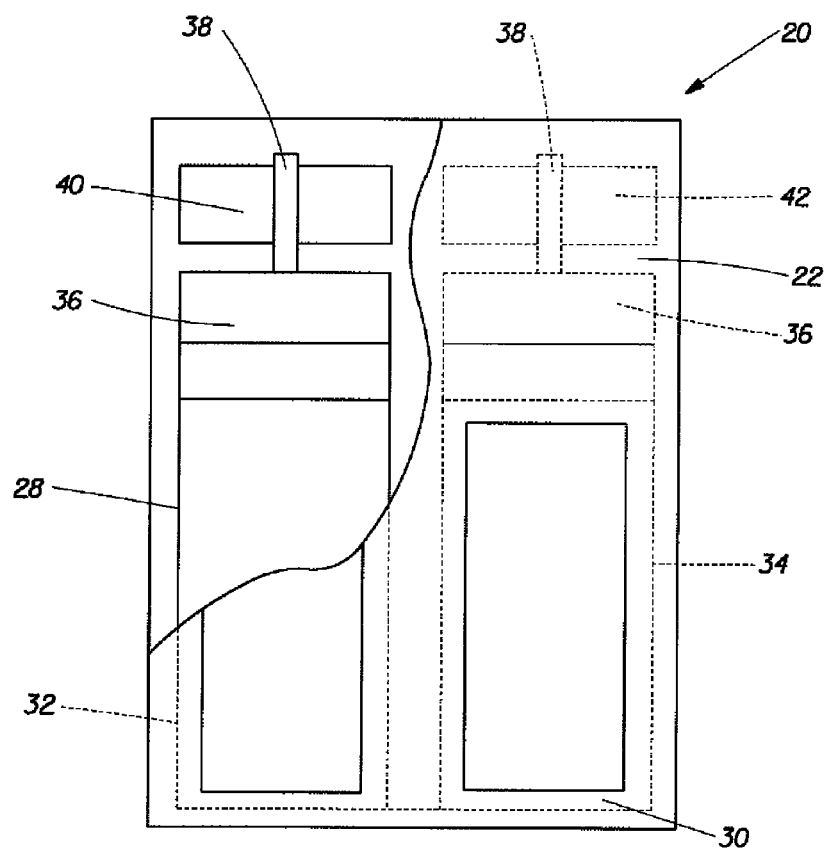
FIG. 6 is a partially fragmented schematic front view showing one non-limiting embodiment of a device for emitting volatile compositions.
Figure 7:
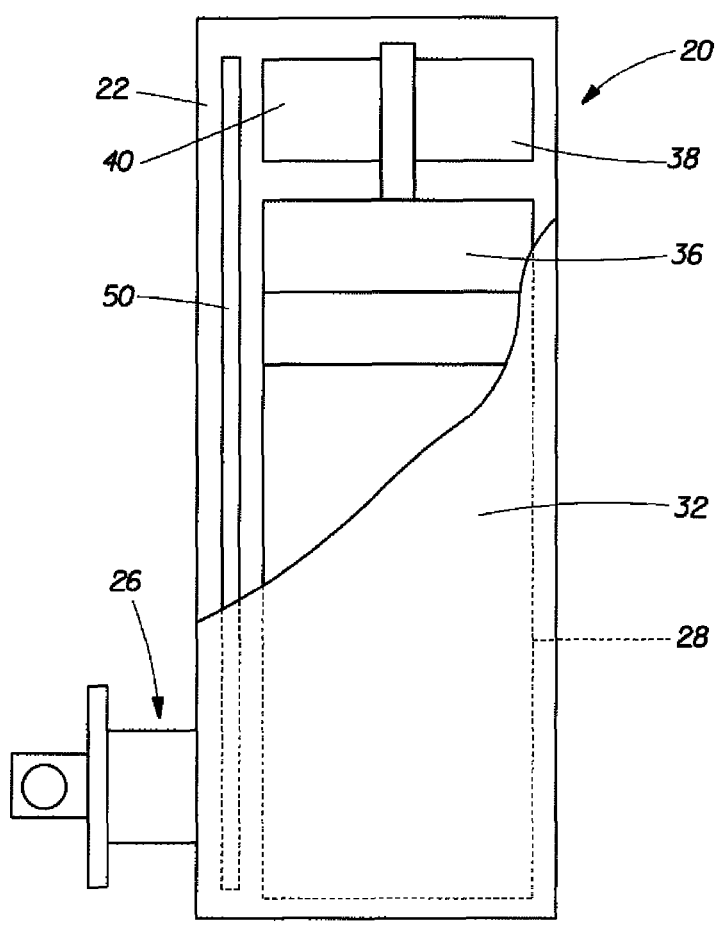
FIG. 7 is a partially fragmented schematic side view of the device shown in FIG. 6.
Figure 8:
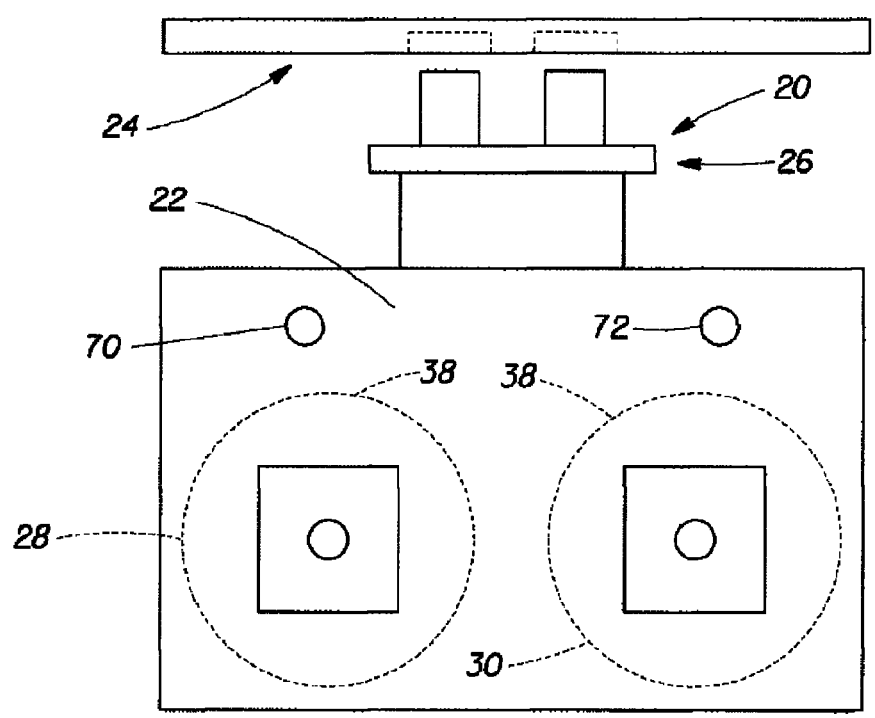
FIG. 8 is a schematic top view of the device shown in FIG. 6, showing the same adjacent to the cover plate of an electrical outlet.

FIGS. 6-8 show one non-limiting embodiment of a device 20 for emitting volatile compositions according to the methods described above. The device can have a pre-selected emission program, which is already programmed when a consumer buys the device, or the device can be provided with a selection of several emission programs and the consumer can select between these programs. In these or other embodiments, the device 20 can use technology similar to the "random play" technology used in compact disc (CD) players to randomly alternate between different volatile materials.

As shown in FIGS. 6-8, the device 20 comprises a housing 22, and the housing 22 is supported on an electrical outlet 24 by a plug 26 that is at least indirectly joined to the housing 22. The device 20 further comprises at least one container, or reservoir. In the embodiment shown in FIGS. 6-8, the device 20 comprises two reservoirs 28 and 30. The reservoirs 28 and 30 contain at least a first volatile composition 32 and a second volatile composition 34. The housing 22 may serve as a holder for the reservoirs 28 and 30 and any of the other components of the device described below.

The reservoirs 28 and 30 can comprise any suitable type of container, and can be made of any suitable material. Suitable materials for the reservoirs include, but are not limited to glass and plastic. The reservoirs 28 and 30 can comprise any type of container that is suitable for holding volatile materials. The reservoirs 28 and 30 may be part of the housing 22, or they may be separate components that are removably joined to a portion of the device 20 such as the housing 22. It is also possible for a single reservoir to hold more than one type of volatile material. Such a reservoir could, for instance, have two or more compartments for volatile materials. In the embodiment shown in FIGS. 6-8, the reservoirs 28 and 30 comprise two separate bottles.

The reservoirs 28 and 30 in FIGS. 6-8 contain volatile compositions in the form of scented perfume oils. The reservoirs further comprise a seal 36 for containing the volatile material, and a wick 38 for dispensing the volatile material. The device 20 and/or the reservoirs 28 and 30 may further comprise an additional seal for covering the wick 38 of one or more of the volatile materials when the volatile material is not being emitted.

The term "volatile compositions" as used herein, refers to a material or a discrete unit comprising of one or more materials that is vaporizable, or comprises a material that is vaporizable. The term "volatile compositions," thus includes (but is not limited to) compositions that are comprised entirely of a single volatile material. The terms "volatile materials," "aroma," "fragrance," and "scents," as used herein, include, but are not limited to pleasant or savory smells, and, thus, also encompass materials that function as insecticides, air fresheners, deodorants, aromacology, aromatherapy, insecticides, or any other material that acts to condition, modify, or otherwise charge the atmosphere or to modify the environment. It should be understood that certain volatile compositions including, but not limited to perfumes, aromatic materials, and scented materials, will often comprise one or more volatile materials (which may form a unique and/or discrete unit comprised of a collection of volatile materials). It should be understood that the term "volatile composition" refers to compositions that have at least one volatile component, and it is not necessary for all of the component materials of the volatile composition to be volatile. The volatile compositions described herein may, thus, also have non-volatile components. It should also be understood that when the volatile compositions are described herein as being "emitted," this refers to the volatilization of the volatile components thereof, and does not require that the non-volatile components thereof be emitted. The volatile compositions of interest herein can be in any suitable form including, but not limited to, solids, liquids, gels, encapsulates, wicks, and carrier materials, such as porous materials impregnated with or containing the volatile material, and combinations thereof.

In the case of scented materials or fragrances, the different scented materials can be similar, related, complementary, or contrasting. It may not be desirable, however, for the scented materials to be too similar if the different scented materials are being used in an attempt to avoid the problem of scent habituation; otherwise, the people experiencing the scents may not notice that a different scent is being emitted. The different scents can be related to each other by a common theme, or in some other manner. For example, the different scents can all be floral, fruit scents, etc. An example of scents that are different, but complementary, might be a vanilla scent and a French vanilla scent.

The present invention also comprises a method of providing choices of compatible volatile compositions, such as fragrance compositions, to consumers. In one embodiment, such a method comprises providing fragrance compositions for use in one or more emitting devices. More specifically, in one embodiment, the method can comprise providing a consumer with a selection of two or more fragrance compositions in reservoirs that are configured for use in one or more emitting devices; and providing some type of indicia to inform a consumer which of the two or more fragrance compositions are compatible for use together. In other embodiments, reservoirs can serve as the emitting devices (e.g., plug-in devices, aerosol cans, etc.). In certain embodiments, the method can pre-select for consumers two or more fragrance compositions that are complementary, yet discernibly different. In other alternative embodiments, the method can comprise selling such different volatile compositions together, such as in bundle packs of (two, three, or more) volatile compositions. Any of the foregoing embodiments may be used in supplying consumers with their initial product(s), as well as with refills for the same. In certain embodiments, the method may comprise supplying consumers with types of volatile compositions other than, or in addition to, fragrance compositions (for example, a fragrance composition and a malodor reducing composition). In some embodiments such a method comprises providing fragrance-dispensing kits, each kit comprising perfume modules that comprise one or more reservoirs, and at least one heated-wick perfume composition-dispensing device that is adapted to receive at least one perfume module. In some embodiments, the kits also include at least one refill perfume module that is not in operable communication with the heated-wick perfume composition-dispensing device.

Wick devices according to the present invention may, in some embodiments, be passive, or ambient devices. The volatile materials are volatilized other than by application of heat. In other embodiments, the wick devices are heated wick devices, as further described herein.

The embodiment of the device 20 shown in FIGS. 6-8 further comprises a mechanism for activating the volatile materials from their "resting" state to an activated state. Such a component may include, but is not limited to, a component that volatilizes or heats the volatile materials. The device 20 may also contain a component, such as a fan, for diffusing or transporting the volatile materials into the environment or atmosphere. In various embodiments, the device 20 may comprise a heater, a fan, or both, or some other type of mechanism.

In the embodiment shown in FIGS. 6-8, the device 20 comprises at least one heating system or heater, such as heaters 40 and 42. The heaters 40 and 42 can comprise any suitable type of heater, and can be located in any suitable location in or relative to the device 20. In the embodiment shown in FIGS. 6-8, the heaters 40 and 42 comprise heating elements that are in the form of circular rings that at least partially surround the wicks 38 protruding from the bottles of the volatile compositions.

The device 20 shown in FIGS. 6-8 further comprises a switching mechanism 50 that changes the volatile material being emitted by the device 20. The switching mechanism 50 can comprise any suitable type of mechanism that causes the device to change the volatile material being emitted. In the embodiment shown, the switching mechanism controls the activation of the heaters so that the heater will be turned on for the volatile material that is desired to be emitted. Suitable switching mechanisms include, but are not limited to, analog timing circuitry, digital circuitry, combinations of analog and digital circuitry, microprocessors, and mechanical actuation switches such as shape memory alloys (NiTi wire) or bimetallic switches.

Figure 9:
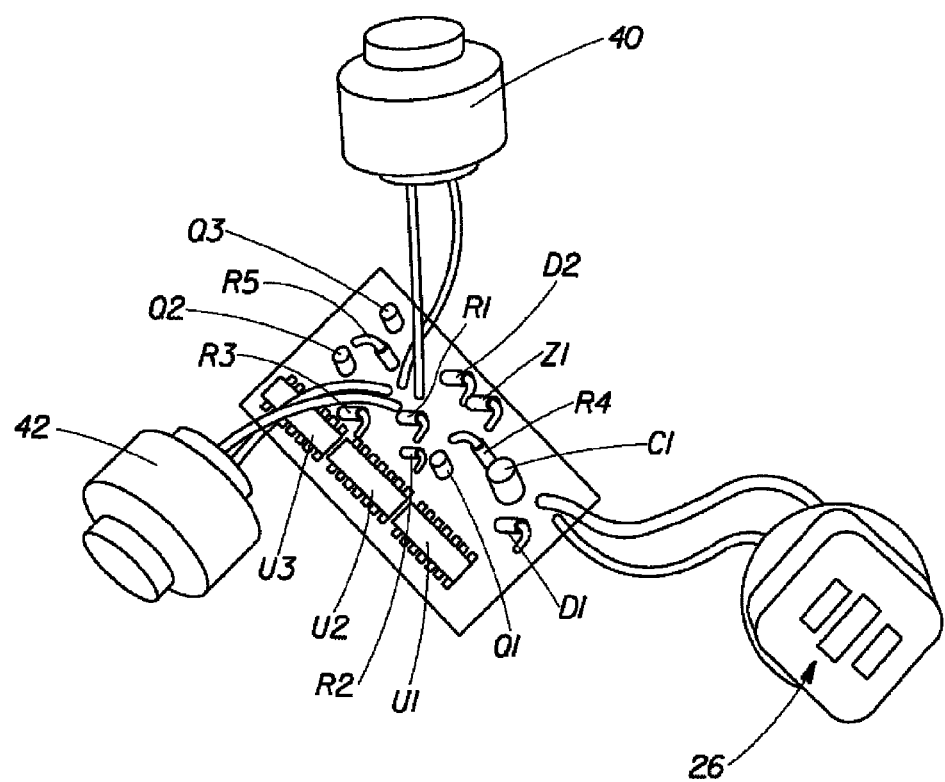
FIG. 9 is a perspective view of a printed circuit board that can be used to control the device shown in FIGS. 6-8, along with the heaters and plug that are attached thereto.

As shown in FIG. 9, in one non-limiting embodiment, the switching mechanism 50 comprises a combination analog and digital circuit in the form of a printed circuit board (or "PCB"). The circuit comprises: a single-sided PC board 52; a capacitor designated C1; a pair of diodes D1 and D2; three transistors Q1, Q2, and Q3; five resistors R1-R5; three counters U1, U2, and U3; a third diode Z1. Any suitable type of heater can be used for heaters 40 and 42, including but not limited to resistance heaters (several types of which are commercially available). The heaters 40 and 42, as well as the wall power plug 26, are also connected to the circuit board 52 by wires 66. Suitable components for circuit are set out in the following table:

TABLE 10

| Reference Number or Letter | Component | Properties |
|---|---|---|
| C1 | Capacitor, Electrolytic | 1 microF, 250 V |
| D1, D2 | Diode | 1N4004, or similar |
| 26 | Wall power plug | |
| Q1, Q2, Q3 | Transistors, NPN | NPN 200 V, 200 mA |
| R1-R5 | Resistors | ⅛ watt |
| U1, U2, U3 | Counters | CD4024, or similar |
| Z1 | Diode, Zener, 11 V | 1N4741A, or similar |

Figure 10:
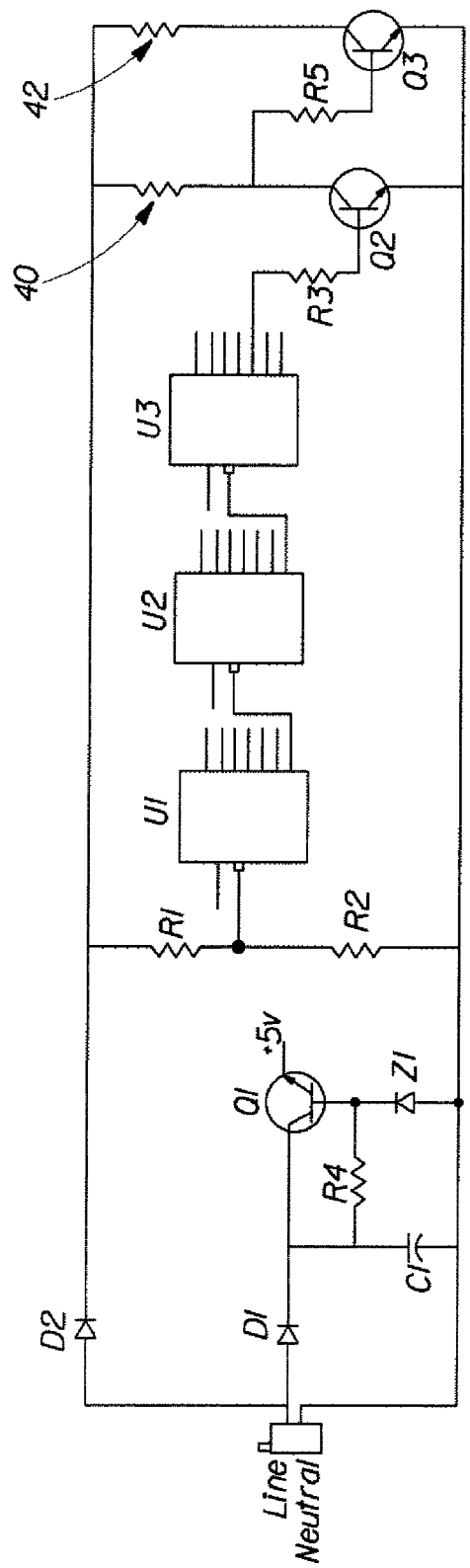
FIG. 10 is a schematic of the circuit shown in FIG. 9.

The components of the circuit may be through-hole or surface mounted. In the embodiment shown, a 38×66 mm single sided PC board 52 with through-hole components is used. The material comprising the PC board 52 can be a standard material such as FR-4 epoxy base fiberglass, but any UL approved material is acceptable. The wall power plug 26 is a molded wall plug with approximately 100 mm pigtails into the PC board. FIG. 10 is a schematic for one example of a circuit. This circuit provides a timing function that alternates current between two paths over a time period of several tens of hours, with a pre-selected time for each heater to be turned on and off.

In other embodiments, the switching mechanism may include, but is not limited to, the following alternative types of switching mechanisms: (1) a magnetic sensor with a pickup that counts the number of rotations of the motor of a fan used to disperse the volatile composition(s) such that after a certain number of rotations, the device will switch from one volatile composition to another; and (2) a device comprising dual shape memory alloys, or bimetallic strips or switches that can complete a circuit at ambient temperature and then cut-off when a certain temperature is reached. The two-way effect can be used since as the temperature lowers, the material can complete the circuit again, thus acting as a thermostat to keep the heater on and then turn it off. The shape memory alloy may serve as the heater as well as the pulse generator.

Figures 11A, 11B:
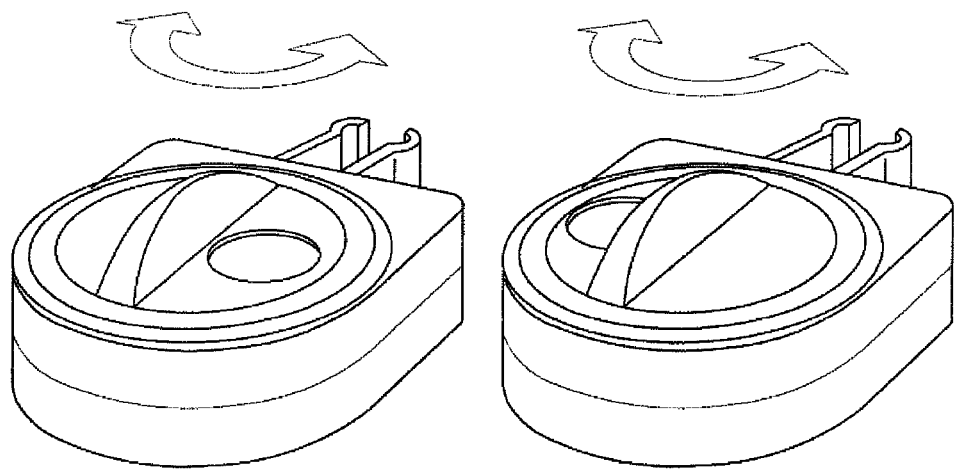
FIG. 11A shows a cap structure which defines a vent hole and a rotatable cover comprising a grip knob.
FIG. 11B shows the cap structure and rotatable cover of FIG. 11A wherein the rotatable cover is rotated to show another vent hole.

Other embodiments of switching mechanisms include movable covers to control the release of one or more volatile compositions. In certain embodiments, the devices for dispensing volatile compositions comprise a cap or other structure which encloses one or more chambers or is otherwise positioned in relation to two or more positions or spaces which are occupied by two or more separate units or modules for dispensing volatile compositions. In other embodiments, the devices for dispensing volatile compositions comprise caps or other structures which cover two or more separate units or modules for dispensing volatile compositions. The cap structures define two or more vent holes or orifices, and optionally comprise vents, louvers or combinations thereof. The cap structures comprise a movable cover which can be automatically or manually moved to cover one or more of the discrete chambers or spaces, to enclose or reveal the two or more separate units or modules for dispensing volatile compositions. In one embodiment, the cover, in use, is moved to alternately cover at least one chamber while exposing the space defined by at least one chamber. Optionally, the cap may have a clip structure which facilitates fixation or positioning of the volatile composition-dispensing device on an architectural structure of a house, or on a piece of furniture or an automobile fixture. FIG. 11 depicts a cap structure which defines two vent holes and a rotatable cover which is manually actuated by the rotation of a knob to selectively expose one or the other, or neither of the vent holes. In some embodiments, the cap structure may be automatically operated. In some embodiments, the device may further comprise a fan in operable communication with the cap structure to facilitate the volatilization of the volatile compositions from within the vented portion or portions of the device or system. Particularly useful volatile composition-dispensing modules and materials for use with devices having cap structures include passive, or unheated, wicks, liquids, slurries, gels, and solid beads.

The device 20 can comprise a number of additional optional features. The device can be provided with indicators so that a person is further made aware that the volatile material being emitted has changed. Such indicators can be visual and/or audible. For example, in the case of scented materials, such an indicator may allow a person to see which scent is being emitted at a given time. In the embodiment shown in FIGS. 6-8, the indicators are in the form of lights 70 and 72. In another example, at least a portion of the device 20 (such as all or a portion of the housing) or the reservoirs may be made of a type of plastic that changes color when heated.

The device can be provided with additional user controls. The device can include an "on/off" switch to allow a user to turn the device on and off without removing it from the electrical socket. The device can be provided with a control that allows the user to control the emission period of one or more of the volatile compositions, and/or the time between the emission of the different volatile compositions, or the time that the volatile materials are emitted during an overlapping time period. For example, in one non-limiting embodiment, if the device is provided with the capability of emitting each volatile material during a period greater than 15 minutes and less than or equal to 48 hours, then the device can be provided with a control that allows the user to set the emission period for one or more of the volatile compositions to 30 minutes, 45 minutes, or 72 minutes, or to one hour, for example.

The device can be provided with additional user controls. The device can comprise a thermostat or other switch to allow a user to adjust the temperature settings of the heat sources for one or more of the volatile compositions. The settings may be predefined for particular volatile compositions, or may be adjustable based on selected temperatures to be applied to a wick.

The device can also be sold in the form of a kit that includes the device and one or more reservoirs of volatile compositions. The device and/or kit can also include instructions for use that instruct the user regarding certain emission periods that may be used to produce certain results, and/or instructions regarding where to place the device in a given space. For example, the instructions may include instructions for setting the device based on the size of the room, vehicle, etc. in which the device is placed. Such instructions may also include instructions to the user to choose more frequent changes between the emissions of scented materials for greater scent awareness. Instructions may also be provided to specify how to operate the device relative to other devices. The instructions can be provided in any suitable form, e.g., written, audio, and/or video.

The device can be battery powered so that it need not be plugged into an electrical outlet. The device can also be configured so that it can be both plugged in and powered by a source of electrical current, and also battery powered. The device can also be provided with an adapter so that it can be plugged into the cigarette lighter in a vehicle. In addition, the device can be provided with a remote control that allows the user to control any, or all, of the emission properties of the device (including, but not limited to changing the volatile material being emitted) without touching the device.

The device may comprise a microprocessor that has less component parts compared to analog circuits, and improved circuit quality from lot to lot. The microprocessor can allow the user to program and control the temperature profile by modulation to alter performance. If desired, the microprocessor may be connected to a user interface. This can be any suitable type of user interface. Examples of types of user interfaces include, but are not limited to LCD screens and LEDs. In addition, the microprocessor enables components to allow multiple devices (such as those located in different parts of a room, or in different rooms), to communicate with each other. For example, the microprocessor can enable a remote control to send digital signals via an infrared beam to turn another device "on" or "off."

Figure 12:
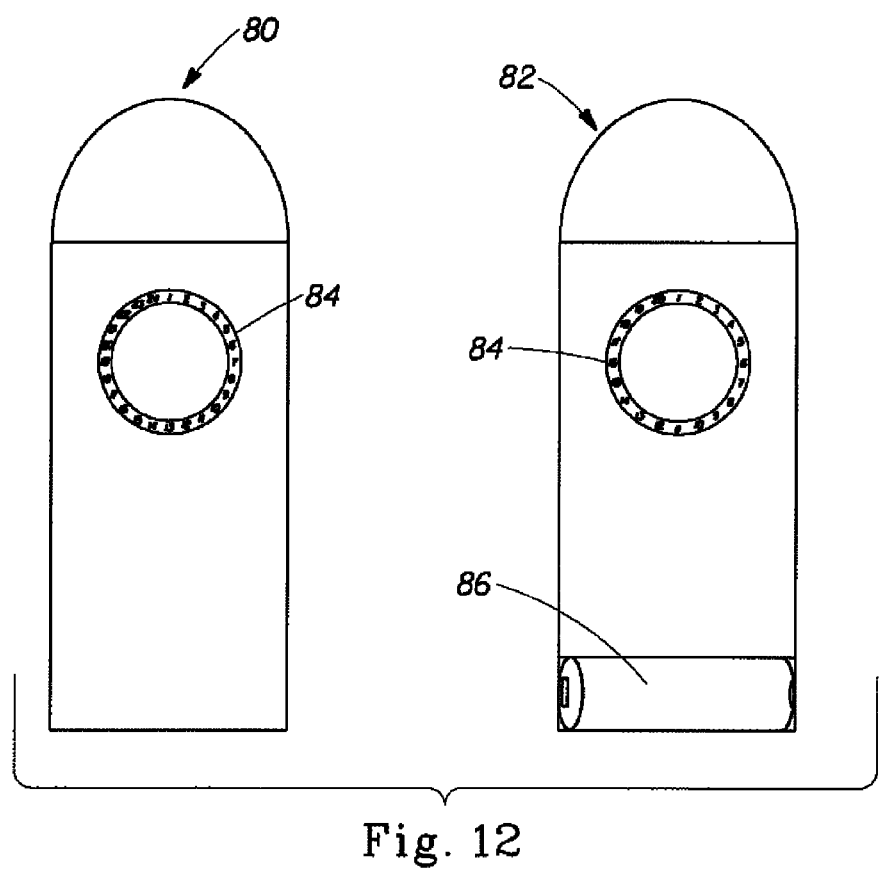
FIG. 12 shows two aerosol devices that operate on timers.
Figure 13:
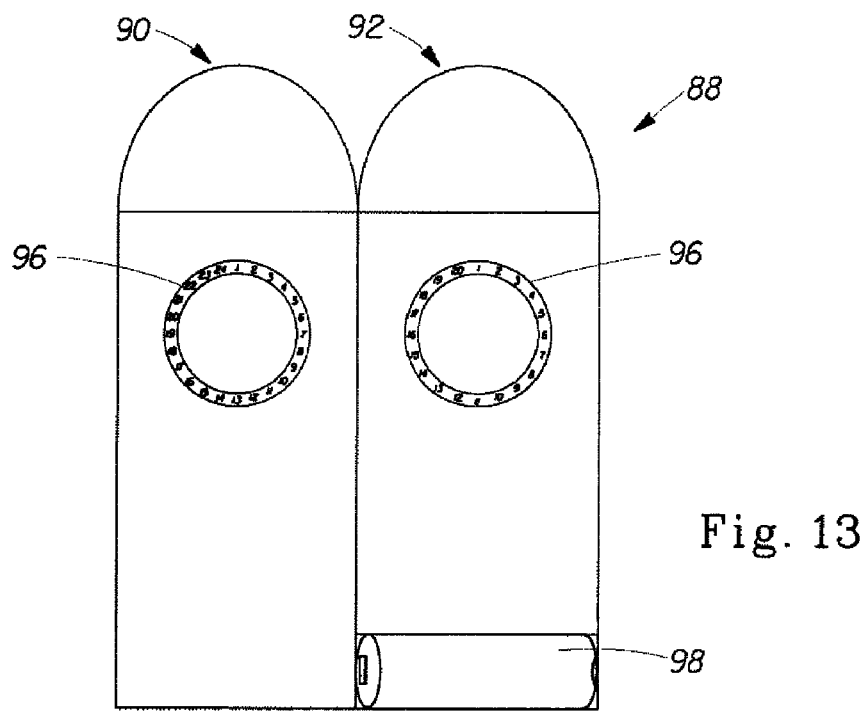
FIG. 13 shows a single device comprising two aerosol containers that operate on timers.

Numerous other types of devices are possible. For example, in other embodiments, the method described herein can be carried out by two or more dispensing devices. Such dispensing devices comprise any type of dispensing device, including, but not limited to aerosol sprayers. FIG. 12 shows one non-limiting embodiment of an arrangement of aerosol sprayers 80 and 82. The aerosol sprayers used in such a method can function in any suitable manner. In some embodiments, the aerosol sprayers may each operate independently, such as on timers 84 so that they alternate the emission of the volatile materials in the manner desired. The dispensing devices can be powered in any suitable manner, such as by a battery 86. The dispensing devices 80 and 82 may be located adjacent to each other, or they may be located in different parts of the space in which it is desired to emit the volatile materials. FIG. 13 shows another non-limiting embodiment of a dispensing device 88. In FIG. 13, the dispensing device 88 is a single device that comprises two (or more) dispensers, such as aerosol sprayers 90 and 92. The device 88 may operate on one or more timers, or sensors 96, and can be powered by one or more batteries, or other power sources.

In some embodiments, the devices can be configured to turn on and off in response to some stimulus, such as by sensors that respond to light, noise and/or motion. For example, one of the devices can be configured to turn on when it senses light, and another device can be set to turn off when it senses light. In another example, a microprocessor can be used with motion sensors to turn on the device (for example, a heater, and/or a fan in the device). For example, the device can be off all the time until a person moves in the vicinity of the motion sensor. The device can then turn on when a person walks in the vicinity of the motion sensor. Using a microprocessor provides flexibility in controlling the characteristics of the emission of the volatile materials. This is because it is possible to replace the microprocessor if it is desired to change the emission characteristics. Replacing the microprocessor eliminates the need to modify the entire circuit.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

EXAMPLES

Example 1

Perfume Evaporation in Plug-Ins Decreases Over Time

It is known in the art that extended exposure to a scent produces an habituation effect, whereby a person is less able to recognize the presence of a particular scent, even if present in the same concentration. This phenomenon occurs with the use of scent-emitting devices that are commercially available.

However, it is believed by the present inventors that, in addition to the habituation phenomenon, reduced scent output over time by commercially available devices even further contributes to lack of user scent recognition. To test this hypothesis, a commercially available product, GLADE® Sky Breeze®, was plugged in (i.e., turned on) and allowed to emit scent for an extended period of time. Evaporation rate (or release rate) was determined by measuring the starting content of the device and taking daily measurements to determine how much was lost.

Figure 14:
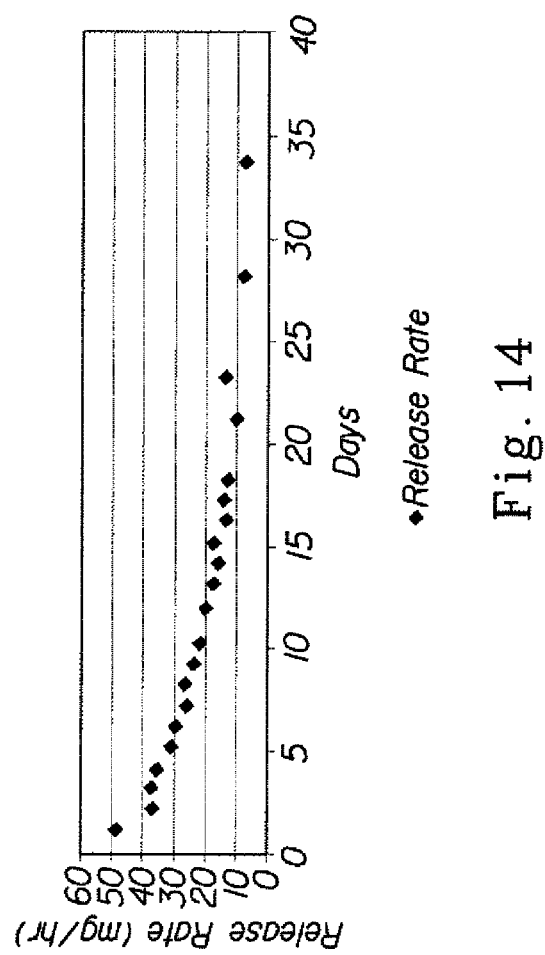
FIG. 14 diagrammatically illustrates how evaporation rate decreases over time.

FIG. 14 shows the results of the study. As can be seen from the Figure, evaporation rate significantly decreases over time. Indeed, evaporation rate had fallen by nearly 50% after only one week of use. Additionally, there is a visible difference in wicks that are used continuously versus toggled. (See FIG. 15, which shows a photo of a wick that was used continuously for 21 days, compared to a photo of a wick toggled on and off for 42 days.)

Example 2

Wick Clogging Causes Decrease in Evaporation Rate

The observed reduction in evaporation rate could have been caused by a number of factors, including selective evaporation of more volatile compounds and clogging of the wick. To determine the mechanistic reasons behind the decrease in evaporation rate, further studies were performed.

Figure 16:
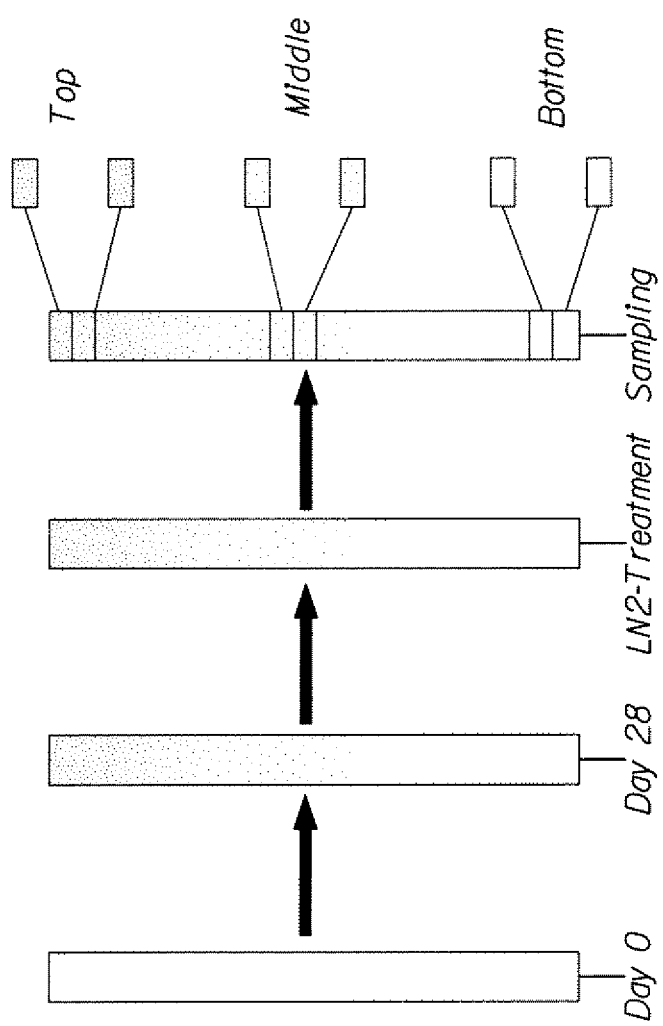
FIG. 16 diagrammatically illustrates what occurs with extended continuous wick use.
Figure 17:
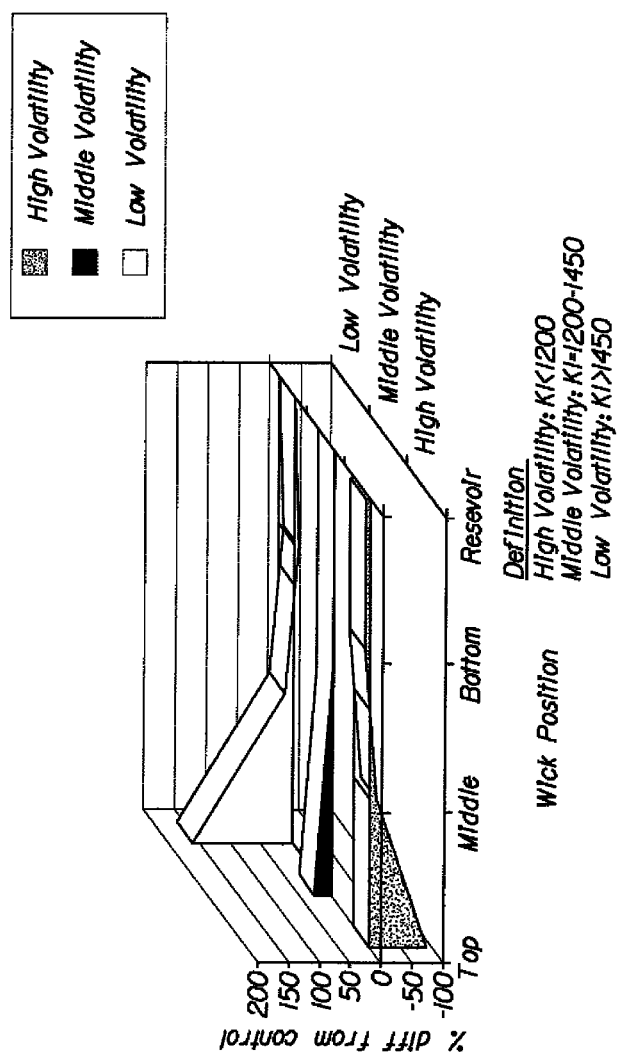
FIG. 17 diagrammatically illustrates how the distribution of composition components changes with time.

GLADE® Vanilla Breeze® and Hawaiian Breeze® perfume devices were turned on for 28 days continuously. At the end of 28 days, the wick was removed from the device and frozen in liquid nitrogen. Samples were taken from the top, middle, and bottom of the wick. At the same time, the volatile composition remaining in the reservoir was sampled. The volatile compositions sampled were analyzed by gas chromatograph and their Kovats indices determined. FIGS. 16 and 17 diagrammatically illustrate the results.

As can be seen from FIG. 16, the wick visibly changes over the testing period. The bottom of the wick is lightest in color and the wick becomes darker toward the top. This is also apparent in the photos in FIG. 15.

FIG. 17 shows exactly what happens during wick clogging. There was almost no difference between the different components in the content of the reservoir: low, middle, and high volatility components differed very little from control, and differed very little from each other. The same was observed for the bottom and middle of the wick.

The top of the wick, however, showed striking differences. High volatility compounds were nearly depleted and middle volatility compounds were slightly higher than control. Most striking, low volatility compounds had collected at the top of the wick more than 150% more than control. The population of volatile compounds at the top of the wick—the primary locus of volatilization—was very highly skewed toward low volatility components. Thus, these low volatility components were effectively controlling the rate of evaporation, in effect "clogging the wick."

Without wishing to be bound by theory, it appears that what is occurring is a build-up of materials having lower volatility at the top of the wick, thereby preventing more volatile materials from moving to the top of the wick and evaporating. At the same time, compounds in the volatile composition that are more volatile are selectively evaporated, further concentrating lower volatility compounds in the top of the wick, and further aggravating the clogging phenomenon. Thus, for a number of reasons that may be additive or even synergistic, evaporation of volatile materials rapidly decreases during prolonged use of a wick device. The energy continually applied to the device, in the form of sustained heat to the wick, drives these less volatile compounds against the concentration gradient, forcing them to accumulate in the top of the wick. The emission from a commercial plug-in product was shown to drop by about 50% during one only one week's use. (See FIG. 14.) By deliberately toggling a heated wick device to the "OFF" position, or introducing a gap between the emissions of a single or multiple wick device, the volatile components diffuse within the wick to reach an equilibrium concentration that approximate the composition of the volatile component mixture in the reservoir. Thus, toggling "OFF," or providing a gap in the emission by removing heat from the wick relives the concentration gradient that "clogs" the wick.

Example 3

Toggling Reduces Clogging and Improves Evaporation Rates

Once it was discovered that the reduction in evaporation rate was caused by wick clogging, steps were taken to solve the problem. It was surprisingly discovered that by allowing the wick-based evaporation device a resting period (generally by reducing the heat applied to the wick), back-flow of volatile materials occurs within the wick, thereby allowing the less volatile components to flow with the concentration gradient and back toward equilibrium. Once the resting period is over, and back-flow of the less volatile components has occurred, energy can be reapplied to the system for a finite period, during which volatilization of the composition again occurs. This cycle can be repeated any number of times.

Figure 18:
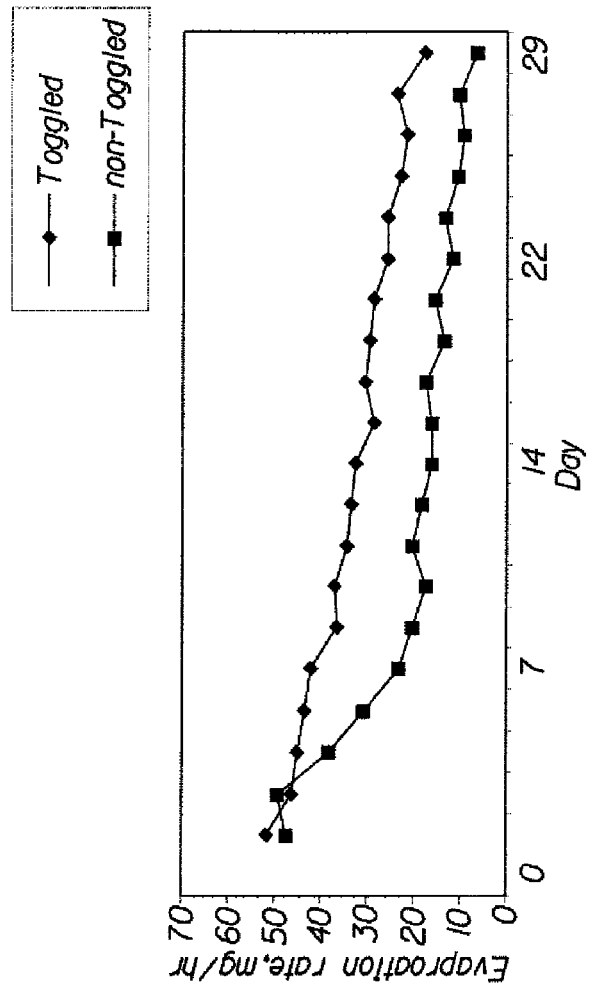
FIG. 18 diagrammatically illustrates the effect of toggling on evaporation rates.

FIG. 18 shows that by toggling a single wick device on and off, an evaporation rate can be improved significantly. Briefly, FIG. 18 shows two evaporation curves for a commercially available product, GLADE® Sky Breeze®, which was activated in two different ways. One device remained on continuously for approximately four weeks ("non-toggled"). The other device was cycled on and off for 72-minute intervals ("toggled") over an eight-week period. (Testing of the toggled device required twice as long, so the "days" axis values were divided by two to achieve a comparable curve.)

Figure 15:
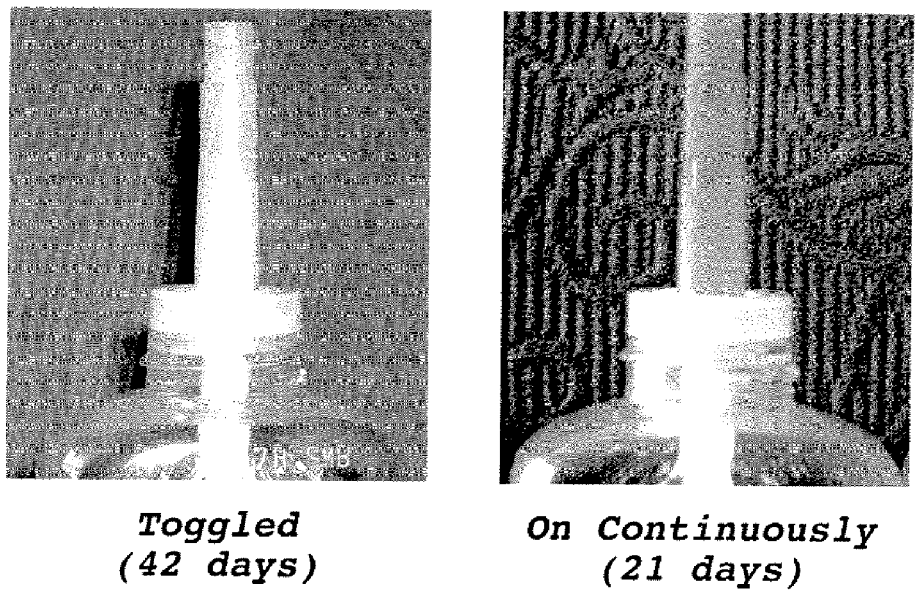
FIG. 15 shows photographs of wicks used continuously or toggled.

As can be seen from FIG. 18, cycling a wick device on and off produces a significant increase in the evaporation rate from the device. The photos in FIG. 15 provide evidence that the on/off cycling significantly reduces the wick clogging.

Example 4

Larger Pore Size Improves Evaporation Profile

Once it was discovered that wick clogging was responsible for reduced evaporation, and that by reducing clogging evaporation could be increased, further steps were taken to identify ways to improve evaporation. This Example shows that by increasing pore size, evaporation is increased.

Figure 19:
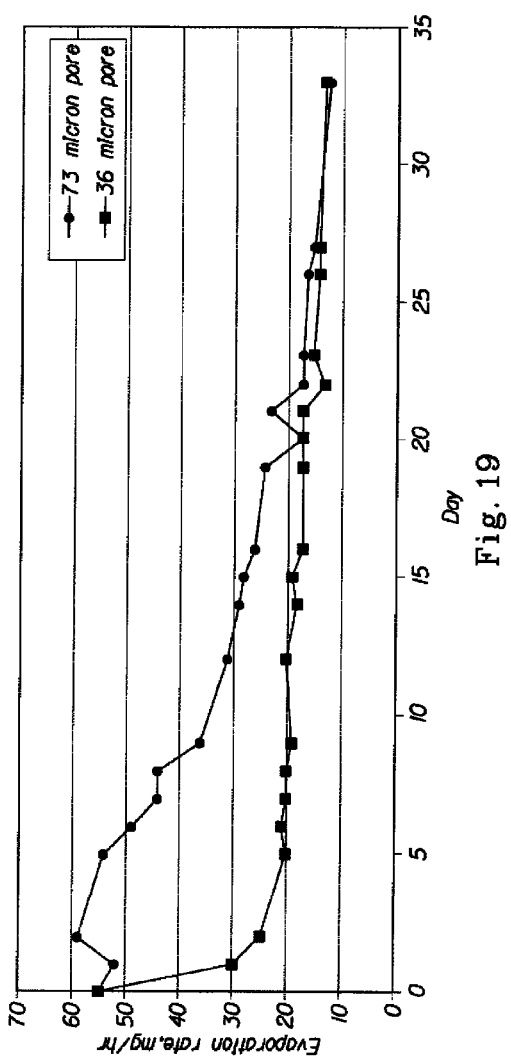
FIG. 19 diagrammatically illustrates the effect of changing wick pore size.

Briefly, an AIR WICK® Country Berries® perfume device was tested using two wicks: a) 36 micron average pore size, and b) 73 micron average pore size. The two wicks were tested by running a device continuously for more than one month by toggling on and off. FIG. 19 shows the results.

As can be seen, within the first week, the higher pore size wick performed significantly better than the smaller pore-size wick. The difference decreased over the second week, and by the third week, there was no difference. It is believed that this convergence at a point of low performance results from wick clogging. The wick clogging occurs in the low pore size wick much earlier than in the larger pore size wick. From these experiments, it can be concluded that a larger pore size wick produces better evaporation than a smaller pore size wick.

Example 5

Shorter Wicks Perform Better

Additional studies were performed to determine if other characteristics of the wick could improve the evaporation profile. This example shows how by decreasing wick length, evaporation can be improved.

Figure 20:
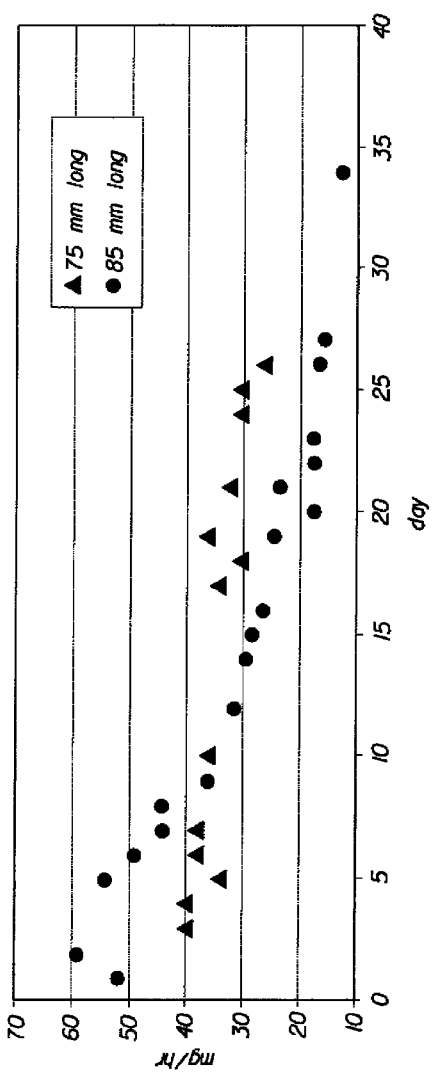
FIG. 20 diagrammatically illustrates the effect of changing wick length.

Briefly, an AIR WICK® Country Berries® perfume device was tested using two 73-micron wicks: a) 75 mm length, and b) 85 mm length. The two wicks were tested by running a device continuously for more than one month. The device was alternately turned on and off for 72-minute periods. During the "on" portion of each cycle, the heater temperature was 70° C. FIG. 20 shows the results.

As can be seen, the shorter wick produced a more stable evaporation profile. After more than three weeks of use, the evaporation had decreased by only about 25%, whereas the evaporation from the longer wick had decreased by more than 50%.

Example 6

Determination of Cycle Time

Additional studies were performed to determine the cycle time that achieved a most desirable scent emission for a two-wick system.

Figure 21A:
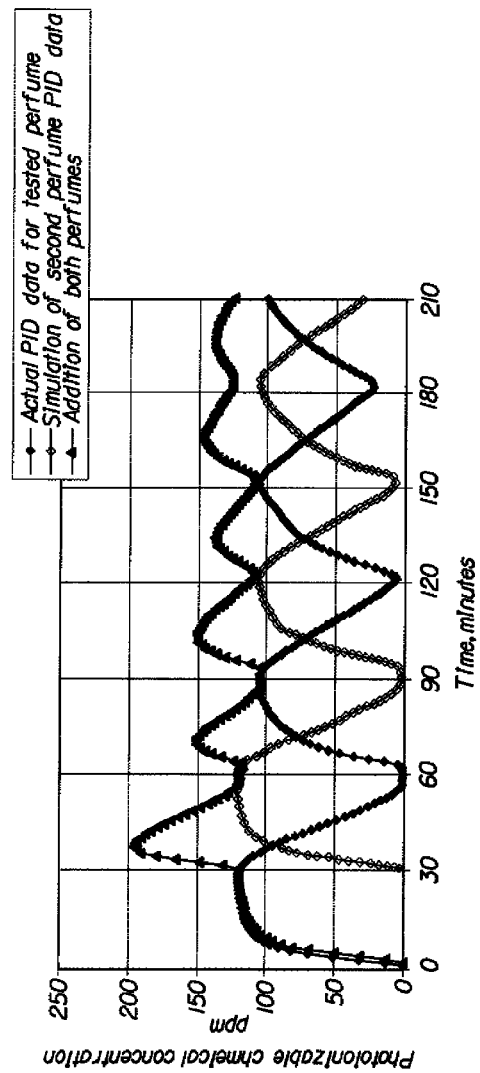
FIG. 21A diagrammatically illustrates the overall scent emission effect of changing the cycle time to every 30 minutes.
Figure 21B:
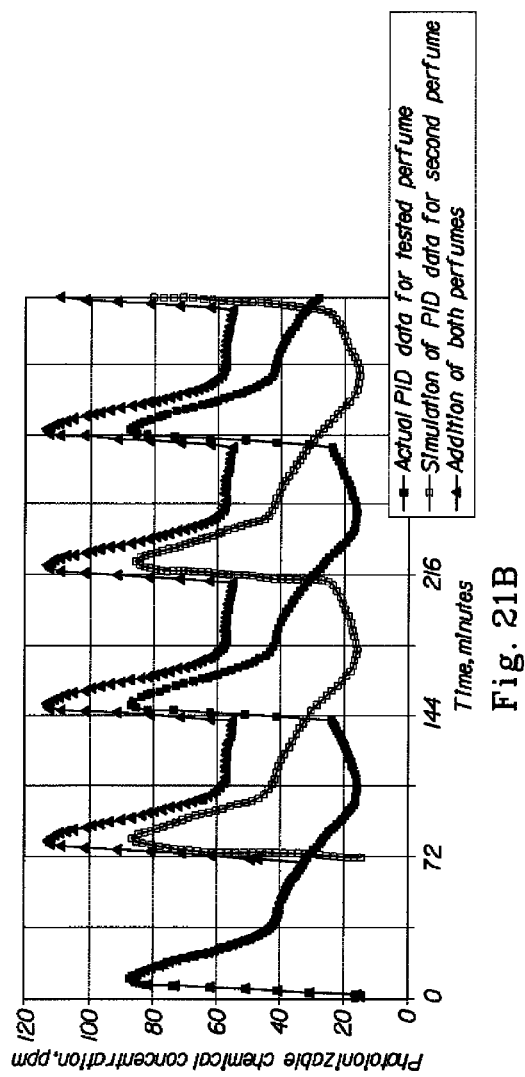
FIG. 21B diagrammatically illustrates the overall scent emission effect of changing the cycle time to every 72 minutes.

Briefly, two AIR WICK® Country Berries® perfume devices were tested. The first was alternately turned on and off for 30-minute periods. The second was alternately turned on and off for 72-minute periods. The emissions were measured using a photoionization detector (PID), Photovac model 2020. The results were plotted versus time. In each case, the recorded results were additionally shifted by 30 and 72 minutes, respectively, to simulate a second, identical, scent-emitting wick. The plots are shown in FIGS. 21A and 21B.

As can be seen from the Figure, a 30-minute cycle time for a two-wick system achieved the most desirable level, i.e., the lowest peak:valley ratio for the simulated combined curve. It should be noted, however, that for a 3-wick system, a longer cycle time would be effective. The theoretical ideal is an infinite number of wicks. Obviously, practicality dictates fewer wicks, and 2, 3, 4, or 5 wicks may be more practical.

Example 7

Determination of Impact of Cycle Time on Volatilization

Additional studies were performed to determine the impact of cycle time on volatilization of perfume compositions from a single wick system.

Briefly, four AIR WICK® Country Berries® perfumes were used in the test. The wicks were made of porous polyethylene with an average pore size of 73 microns, an average pore volume of 38%, and were 85 mm in length with a diameter of 6.8 mm. During the "on" portion of each cycle, the heater temperature was 70° C. and yielded an average wick temperate of 60° C. based on temperature measurements at the top (heated portion) of the wick (a temperature probe was placed at the top of the wick.) The first device was alternately turned on and off for 15-minute periods. The second device was alternately turned on and off for 30-minute periods. The third device was alternately turned on and off for 45-minute periods. The fourth device was alternately turned on and off for 72-minute periods. The emissions were measured using a photoionization detector (PID), Photovac model 2020. The test location was a ten by ten foot room with ambient temperature and airflow.

Emissions were tested for each wick after the devices had been in use for two weeks, and then after the devices had been in use for four weeks. A PID sensor was positioned approximately 5 mm above the top center portion of each wick. Emissions were sampled at peak emission (initial emission after heat is applied to the wick) and once per minute throughout three complete on/off cycles. For example, emissions were sampled for the third device at two weeks, once per minute, for a total sample time of 270 minutes; emissions were again sampled for the first device at four weeks, once per minute, for a total sample time of 270 minutes. Electronic readings from the PID were captured and evaluated for average concentration of perfume at the top of the wick in parts per million during the measured periods. Results of one such study are shown in Table 11.

TABLE 11

Impact of Cycle Time on Wick Evaporation: PID Concentration of Chemical at Wick Surface, average PPM/per minute

| | Wick Age | | | |
| --- | --- | --- | --- | --- |
| | 2 weeks | | 4 weeks | |
| Toggle time | stabilized | peak | stabilized | peak |
| 15 min | 45 | 50 | | |
| 30 min | 100 | 140 | 55 | 65 |
| 45 min | 95 | 125 | NA | NA |
| 72 min | | | 60 | 110 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of emitting a perfume from a heated-wick device comprising the steps:
   a) providing said heated-wick device comprising a first perfume composition in fluid communication with a first wick and a second perfume composition in fluid communication with a second wick;
   b) applying heat to said first wick;
   c) reducing the heat to said first wick;
   d) maintaining reduced heat to said first wick for about 20 minutes to about 48 hours;
   e) applying heat to said second wick;
   f) reducing the heat to said second wick; and
   g) maintaining reduced heat to said second wick for about 20 minutes to about 48 hours.

2. The method according to claim 1, wherein the wick temperature sufficient to increase the rate of volatilization of at least one component of said first perfume composition is greater than or equal to about 40° C.

3. The method according to claim 2, wherein the wick temperature sufficient to increase the rate of volatilization of the at least one component of said first perfume composition is greater than or equal to about 60° C.

4. The method according to claim 3, wherein the wick temperature sufficient to increase the rate of volatilization of the at least one component of said first perfume composition is greater than or equal to about 80° C.

5. The method according to claim 1, wherein the wick temperature sufficient to decrease the rate of volatilization of at least one component of said first perfume composition is less than or equal to about 40° C.

6. The method according to claim 1, wherein the difference between wick temperatures at b) and e) is from about 10° C. to about 100° C.

7. The method according to claim 6, wherein the difference between wick temperatures at b) and e) is from about 20° C. to about 80° C.

8. The method according to claim 7, wherein the difference between wick temperatures at b) and e) is from about 40° C. to about 60° C.

9. The method according to claim 1, wherein steps b) through g) are each repeated at least two times.

10. The method according to claim 1, wherein in said heating step of e), the temperature of said second wick is higher than in the previous heating step of b).

11. The method according to claim 1, wherein performance of steps b) and c) overlaps for a period of from about 0.1% to about 25% of the duration of step e).

12. The method according to claim 1, wherein the performance of steps b) and c) does not overlap.

13. The method according to claim 12, wherein there is a gap between performance of steps b) and e) for a period of from about 0.1% to about 100% of the duration of step b).

14. The method according to claim 1, wherein the reduced heat to the first wick is maintained for a time sufficient to allow for back-flow of all components of the first perfume composition.

15. The method according to claim 1, wherein step b) further comprises applying a fan to the first wick for enhancing release of at least one component of the first perfume composition.

16. The method according to claim 1, wherein said first and second wick have an average pore size of about 50-150 microns.

* * * * *